(12) United States Patent
Burckbuchler et al.

(10) Patent No.: US 11,166,896 B2
(45) Date of Patent: Nov. 9, 2021

(54) PROCESS FOR DYEING AND RELAXING CURLS OF KERATIN FIBRES, USING REDUCING AGENTS AND HAIR DYES, AND ASSOCIATED KIT

(71) Applicant: L'OREAL, Paris (FR)

(72) Inventors: Virginie Burckbuchler, Aulnay-Sous-Bois (FR); Henri Samain, Bievres (FR)

(73) Assignee: L'Oreal, Paris (FR)

( * ) Notice: Subject to any disclaimer, the term of this patent is extended or adjusted under 35 U.S.C. 154(b) by 210 days.

(21) Appl. No.: 16/472,824

(22) PCT Filed: Dec. 22, 2017

(86) PCT No.: PCT/EP2017/084297
§ 371 (c)(1),
(2) Date: Jun. 21, 2019

(87) PCT Pub. No.: WO2018/115393
PCT Pub. Date: Jun. 28, 2018

(65) Prior Publication Data
US 2020/0085714 A1  Mar. 19, 2020

(30) Foreign Application Priority Data
Dec. 22, 2016 (FR) .................................. 1663189

(51) Int. Cl.
| | | |
|---|---|---|
| *A61Q 5/10* | (2006.01) | |
| *A61K 8/46* | (2006.01) | |
| *A45D 7/06* | (2006.01) | |
| *A61K 8/34* | (2006.01) | |
| *A61K 8/41* | (2006.01) | |
| *A61K 8/49* | (2006.01) | |
| *A61Q 5/04* | (2006.01) | |
| *A61Q 5/06* | (2006.01) | |
| *A45D 7/00* | (2006.01) | |

(52) U.S. Cl.
CPC ................. *A61K 8/46* (2013.01); *A45D 7/06* (2013.01); *A61K 8/347* (2013.01); *A61K 8/418* (2013.01); *A61K 8/466* (2013.01); *A61K 8/4926* (2013.01); *A61Q 5/04* (2013.01); *A61Q 5/065* (2013.01); *A61Q 5/10* (2013.01); *A45D 2007/001* (2013.01); *A61K 2800/432* (2013.01); *A61K 2800/884* (2013.01)

(58) Field of Classification Search
CPC . A61Q 5/10; A61Q 5/065; A61Q 5/04; A61K 2800/884; A61K 8/466; A61K 8/418; A61K 2800/432; A61K 8/4926; A61K 8/347; A61K 8/46; A45D 2007/001; A45D 7/06

USPC .............................................. 8/405; 132/206
See application file for complete search history.

(56) References Cited

U.S. PATENT DOCUMENTS

| | | | |
|---|---|---|---|
| 2,890,094 A | 6/1959 | Tucker | |
| 2006/0080791 A1* | 4/2006 | Daubresse | A61K 8/4926 8/405 |
| 2008/0235883 A1* | 10/2008 | Lagrange | A61K 8/4966 8/435 |
| 2009/0019645 A1* | 1/2009 | Plos | A61Q 5/065 8/405 |
| 2009/0126125 A1* | 5/2009 | Greaves | A61Q 5/10 8/407 |
| 2009/0172897 A1* | 7/2009 | Daubresse | C09B 23/145 8/426 |
| 2009/0211038 A1* | 8/2009 | Greaves | A61K 8/4933 8/407 |
| 2012/0266392 A1* | 10/2012 | Greaves | C09B 49/12 8/405 |
| 2013/0283544 A1* | 10/2013 | Greaves | A61K 8/49 8/405 |
| 2014/0075687 A1* | 3/2014 | Guerin | A61K 8/49 8/405 |
| 2014/0137342 A1* | 5/2014 | Guerin | A61Q 5/10 8/405 |

FOREIGN PATENT DOCUMENTS

| | | |
|---|---|---|
| DE | 10360204 A1 | 7/2005 |
| EP | 2191864 A1 | 6/2010 |
| WO | 2015198923 A1 | 12/2015 |

OTHER PUBLICATIONS

International Search Report for corresponding International Application No. PCT/EP2017/084297, 5 pages.

* cited by examiner

*Primary Examiner* — Eisa B Elhilo
(74) *Attorney, Agent, or Firm* — Christensen O'Connor Johnson Kindness PLLC

(57) ABSTRACT

The present invention relates to a process for dyeing and relaxing curls of keratin fibres, such as the hair, which comprises the application to the fibres of one or more acidic compositions comprising reducing agents and of one or more compositions comprising hair-dyeing agents, and a step of heat treatment of the fibres by means of a heating tool. A subject of the invention is also the use of the composition(s) comprising reducing agents and of the composition(s) comprising hair-dyeing agents in a process for dyeing and relaxing curls of keratin fibres. Finally, a subject of the invention is a multi-compartment device or "kit" suitable for carrying out such a process.

25 Claims, No Drawings

PROCESS FOR DYEING AND RELAXING CURLS OF KERATIN FIBRES, USING REDUCING AGENTS AND HAIR DYES, AND ASSOCIATED KIT

The present invention relates to a process for dyeing and relaxing curls of keratin fibres, such as the hair, which comprises the application to the fibres of one or more compositions comprising reducing agents and of one or more compositions comprising hair dyes, and a step of heat treatment of the fibres by means of a heating tool.

A subject of the invention is also the use of the composition(s) comprising reducing agents and of the composition(s) comprising direct dyeing agents in a process for dyeing and relaxing curls of keratin fibres.

Finally, a subject of the invention is a multi-compartment device or "kit" suitable for carrying out such a process.

Many people are not satisfied by the colour and appearance of their hair. In particular, people who have curly hair usually seek to obtain straight hair. Furthermore, these people also seek to modify the colour of their hair, and in particular to dye it, for example in order to mask their grey hair.

To obtain permanent reshaping of the hair such as straightening of the hair, uncurling or relaxing of curls, the technique most commonly used consists, in a first stage, in opening the —S—S— disulfide bonds of keratin (keratocystine) by means of a generally basic composition containing a sulfur-comprising reducing agent (reduction step), and then, after having rinsed the head of hair thus treated, generally with water, in reconstituting, in a second stage, said disulfide bonds by applying to the hair, which has been placed under tension beforehand, an oxidizing composition (oxidation step, also known as the fixing step) so as finally to give the hair the desired shape.

The new shape given to the hair by such a chemical treatment is eminently long-lasting and especially withstands washing with water or shampoos, as opposed to the simple standard techniques of temporary reshaping, such as hairsetting.

Many products intended for uncurling the hair or for relaxing curls exist on the market.

The products intended for uncurling are generally formulated either using very alkaline compositions, at a pH above 12, or using a high concentration of thiols, such as mercaptan compounds.

The oxidizing compositions required for performing the fixing step are usually compositions based on aqueous hydrogen peroxide solution.

However, the application of these products is generally long, with a longer or shorter leave-on time depending on the product, the type of hair and the desired effect. It requires a precise know-how, which is mainly due to the high contents of reducing agents used in the reducing compositions or to the high contents of hydroxides and/or to the very alkaline pH of uncurling compositions, and also to the various more or less long leave-on times of these compositions.

It has also been found that the use of these reducing agents or of these strong alkaline agents can lead to scalp discomfort (irritation, itching, etc.).

Moreover, the compositions employed often pose problems of odours, in particular the reducing compositions and especially those containing thiols. Hair treated with these compositions can also retain an unpleasant odour.

Furthermore, reducing agents are generally used in high concentrations, which may lead to more or less pronounced degradation of the keratin fibre, in particular when the hair is dyed.

These techniques can thus create, in the long term, a detrimental modification of the quality of the hair, leading to a decrease in its cosmetic properties, such as its vitality or its sheen, and a degradation in its mechanical properties, more particularly in its mechanical strength.

Thus, a process capable of performing both dyeing of keratin fibres and relaxing of curls is sought.

In parallel, this process must retain good performance levels on keratin fibres, in particular with an effect that is persistent with respect to several shampooing operations.

Two main methods exist for dyeing human keratin fibres.

The first type of dyeing is "permanent" or oxidation dyeing, which uses dye compositions containing oxidation dye precursors, generally referred to as oxidation bases. This type of dyeing cannot be carried out in a reducing environment.

The second type of dyeing is "semi-permanent" dyeing or direct dyeing, which consists in applying, to the keratin fibres, direct dyes, which are coloured and colouring molecules that have an affinity for said fibres, in leaving them on for a time, and then in rinsing them off. In order to perform these dyeing operations, the direct dyes generally used are chosen from nitrobenzene, anthraquinone, nitropyridine, azo, xanthene, acridine, azine and triarylmethane direct dyes, and natural dyes.

However, the use of a reducing agent for obtaining the effect of relaxing curls requires the opening of disulfide bridges on the keratin fibre, which leads to difficulties in subsequently dyeing the keratin fibre, due in particular to the fact that the reducing agent generally degrades the dyeing agent.

Consequently, there is a need to develop new compositions which make it possible both to dye keratin fibres and to relax curls.

Furthermore, it is desirable for these treatments to be easy to apply, and comfortable for the operator to use, in particular in terms of odours resulting from the implementation of such a process.

It is difficult to dye and at the same time uncurl keratin fibres without detrimentally modifying the colour, in particular in terms of chromaticity or of intensity of the colouration and of persistence in particular with respect to shampooing operations. Furthermore, it is difficult to keep an intense and chromatic colour after passing a straightening iron over the hair, which can cause the colour to deteriorate. Another difficulty is to manage, in the processes, to obtain dyeing and uncurling in which the colour remains uniform from the root to the end.

The applicant has now discovered that the implementation of a particular process in at least three steps makes it possible to meet the abovementioned objectives.

It has thus discovered, surprisingly, a process which combines dyeing and relaxing of curls of keratin fibres, in particular human keratin fibres such as the hair, in several steps, which comprises:

i) the application to said fibres of an acidic composition (A), having a pH of inclusively between 1 and 5 and containing one or more thiol-comprising reducing agents;

ii) the application to said fibres of a composition (B) containing one or more dyes chosen from a) direct dyes and b) oxidation dyes, preferably direct dyes, followed iii) by a step of heat treatment of the fibres by means of a heating tool;

it being understood that steps i) and ii) are carried out separately i) then ii) or else ii) then i) or together on the keratin fibres. Preferably, the steps of the process are carried out according to the following order i) then ii) then iii).

This process makes it possible to achieve the desired properties, inter alia in terms of colouration, of quality and of cosmeticity of the keratin fibres, while at the same time obtaining relaxing of curls of keratin fibres of good and long-lasting quality on the dyed hair.

Furthermore, unexpectedly, the colour obtained remains chromatic, and resistant to the various external attacks, including light, sweat, bad weather, and in particular shampooing operations. Furthermore, the colours obtained are aesthetic, vivid and uniform.

A subject of the present invention is thus a process for dyeing and relaxing curls of keratin fibres, in particular keratin fibres such as the hair, comprising the steps i), ii) and iii) as defined previously.

The implementation of this process makes it possible to obtain a relaxing of curls of keratin fibres which is of good quality and is persistent with respect to several shampooing operations, while at the same time providing colouration of the keratin fibres, in particular of grey hair. Furthermore, the implementation of this method makes it possible to provide the keratin fibres with good cosmetic properties, in particular sheen and softness to the touch.

A subject of the invention is also a kit suitable for implementing the process of the invention. This kit comprises at least two compartments:
  a first compartment comprising an acidic composition (A), at a pH of inclusively between 1 and 5, which comprises one or more thiol-comprising reducing agents;
  a second compartment comprising a composition (B) which comprises one or more direct dyes and
  optionally, a third compartment comprising a composition (C) which comprises one or more non-thiol-comprising reducing agents.

The term "pH of inclusively between 1 and 5" is understood to mean that the limits 1 and 5 are included in the pH range.

A subject of the present invention is also a composition containing at least of the compositions (A) and (B) and also the use of the compositions (A) and (B) in a process for dyeing and shaping and relaxing curls of keratin fibres, in particular human keratin fibres such as the hair.

Such a process is rapid and simple to perform, and does not require any particular know-how.

By virtue of its protection of the integrity of keratin fibres, the implementation of this process makes it possible to give them good cosmetic properties, in particular of colouration, sheen and softness to the touch.

Finally, the process according to the invention makes it possible to substantially reduce the uncomfortable odours resulting from the implementation of a conventional process for relaxing curls.

Other characteristics and advantages of the invention will emerge more clearly on reading the description and the examples that follow.

For the purposes of the present invention and unless otherwise indicated:
  the term "(hetero)aryl" is intended to mean aryl or heteroaryl groups;
  the "aryl" or "heteroaryl" radicals or the aryl or heteroaryl part of a radical may be substituted with at least one substituent borne by a carbon atom, chosen from:
    a $C_1$-$C_6$, and preferably $C_1$-$C_4$, alkyl radical, optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals which may be identical or different; optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
    a halogen atom;
    a hydroxyl or thiol group;
    a $C_1$-$C_6$ alkoxy or $C_1$-$C_6$ alkylthio radical;
    a (poly)hydroxy($C_2$-$C_6$)alkoxy radical;
    an amino radical;
    a 5- or 6-membered heterocycloalkyl radical, preferentially morpholino, piperazino, piperidino or pyrolidino, which is optionally substituted with a ($C_1$-$C_4$) alkyl radical, preferentially methyl;
    a 5- or 6-membered heteroaryl radical, preferentially imidazolyl, optionally substituted with a ($C_1$-$C_4$) alkyl radical, preferentially methyl;
    an amino radical substituted with one or two identical or different $C_1$-$C_6$ alkyl radicals, optionally bearing at least:
      i) a hydroxyl group,
      ii) an amino group optionally substituted with one or two optionally substituted $C_1$-$C_3$ alkyl radicals, said alkyl radicals possibly forming with the nitrogen atom to which they are attached a saturated or unsaturated, optionally substituted 5- to 7-membered heterocycle, optionally comprising at least one other nitrogen or non-nitrogen heteroatom,
      iii) a quaternary ammonium group —N$^+$R'R"R''', M$^-$ for which R', R" and R''', which may be identical or different, represent a hydrogen atom or a $C_1$-$C_4$ alkyl group and M$^-$ represents an anionic counterion,
      iv) or an optionally cationic 5- or 6-membered heteroaryl radical, preferentially imidazolium, optionally substituted with a ($C_1$-$C_4$)alkyl radical, preferentially methyl;
    an acylamino radical (—N(R)—C(O)—R') in which the R radical is a hydrogen atom or a $C_1$-$C_4$ alkyl radical optionally bearing at least one hydroxyl group and the R' radical is a $C_1$-$C_2$ alkyl radical;
    a carbamoyl radical (($R$)$_2$N—C(O)—) in which the R radicals, which may be identical or different, represent a hydrogen atom or a $C_1$-$C_4$ alkyl radical optionally bearing at least one hydroxyl group;
    an alkylsulfonylamino radical (R'—S(O)$_2$—N(R)—) in which the R radical represents a hydrogen atom or a $C_1$-$C_4$ alkyl radical optionally bearing at least one hydroxyl group and the R' radical represents a $C_1$-$C_4$ alkyl radical, or a phenyl radical;
    an aminosulfonyl radical (($R$)$_2$N—S(O)$_2$—) in which the R radicals, which may be identical or different, represent a hydrogen atom or a $C_1$-$C_4$ alkyl radical optionally bearing at least one hydroxyl group;
    a carboxyl radical in the acid or salified form (preferably salified with an alkali metal or a substituted or unsubstituted ammonium);

a cyano group;

a nitro or nitroso group;

a polyhaloalkyl group, preferably trifluoromethyl;

the cyclic or heterocyclic part of a non-aromatic radical may be substituted with at least one substituent chosen from the following groups:

hydroxyl;

$C_1$-$C_4$ alkoxy, $C_2$-$C_4$ (poly)hydroxyalkoxy;

$C_1$-$C_4$ alkyl;

alkylcarbonylamino (R—C(O)—N(R')—) in which the radical R' is a hydrogen atom or a $C_1$-$C_4$ alkyl radical optionally bearing at least one hydroxyl group, and the radical R is a $C_1$-$C_2$ alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R—X—C(O)—) in which the radical R is a $C_1$-$C_4$ alkoxy radical, X is an oxygen atom or an amino group optionally substituted with a $C_1$-$C_4$ alkyl group itself optionally bearing at least one hydroxyl group, said alkyl radical possibly forming with the nitrogen atom to which it is attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups;

a hydrocarbon-based chain is unsaturated when it comprises one or more double bonds and/or one or more triple bonds;

an "aryl" radical represents a monocyclic or fused or non-fused polycyclic carbon-based group, comprising from 6 to 22 carbon atoms, at least one ring of which is aromatic; preferentially, the aryl radical is a phenyl, biphenyl, naphthyl, indenyl, anthracenyl or tetrahydronaphthyl;

a "heteroaryl radical" represents a fused or non-fused, optionally cationic, 5- to 22-membered monocyclic or polycyclic group, comprising from 1 to 6 heteroatoms chosen from nitrogen, oxygen, sulfur and selenium atoms, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthinyl or thioxanthinyl;

a "heterocyclic radical" is a fused or non-fused, 5- to 22-membered monocyclic or polycyclic non-aromatic radical, possibly containing one or two unsaturations and comprising from 1 to 6 heteroatoms chosen from nitrogen, oxygen, sulfur and selenium;

an "alkyl" radical is a linear or branched, saturated $C_1$-$C_{10}$, in particular $C_1$-$C_8$, more particularly $C_1$-$C_6$ and preferably $C_1$-$C_4$, hydrocarbon-based radical;

an "alkoxy" radical is an "alkyl-oxy" radical in which the alkyl part is as defined previously;

an "alkenyl" radical is a linear or branched $C_2$-$C_{10}$, in particular $C_2$-$C_8$, more particularly $C_2$-$C_6$, preferably $C_2$-$C_4$, hydrocarbon-based radical comprising one or more conjugated or non-conjugated unsaturations, preferably comprising one or two double bonds, such as ethylenyl;

the expression "optionally substituted" attributed to the alkyl or alkenyl radical is intended to mean that said alkyl or alkenyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming, with the nitrogen atom that bears them, a 5- to 7-membered heterocycle, optionally comprising another nitrogen or non-nitrogen heteroatom; v) carboxy; vi) or aryl such as phenyl optionally substituted with one or more (di)($C_1$-$C_4$)(alkyl)amino groups or hydroxyl groups;

an "alkoxy" radical is an alkyl-oxy radical for which the alkyl radical is a linear or branched $C_1$-$C_8$ and preferentially $C_1$-$C_6$ hydrocarbon-based radical;

when the alkoxy group is optionally substituted, this implies that the alkyl group is optionally substituted as defined above;

the term "organic or mineral acid salt" is more particularly intended to mean salts chosen from a salt derived from i) hydrochloric acid HCl, ii) hydrobromic acid HBr, iii) sulfuric acid $H_2SO_4$, iv) alkylsulfonic acids: Alk-S(O)$_2$OH such as methanesulfonic acid and ethanesulfonic acid; v) arylsulfonic acids: Ar—S(O)$_2$OH such as benzenesulfonic acid and toluenesulfonic acid; vi) citric acid; vii) succinic acid; viii) tartaric acid; ix) lactic acid; x) alkoxysulfinic acids: Alk-O—S(O)—OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)$—OH; xiv) triflic acid $CF_3SO_3H$; and xv) tetrafluoroboric acid $HBF_4$;

the term "anionic counterion" is intended to mean an anion or an anionic group derived from an organic or mineral acid which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-S(O)$_2$O⁻ such as methylsulfonate or mesylate and ethylsulfonate; iv) arylsulfonates: Ar—S(O)$_2$O⁻ such as benzenesulfonate and toluenesulfonate or tosylate; v) carboxylates Alk-C(O)—OH with Alk representing a ($C_1$-$C_6$)alkyl group optionally substituted with one or more hydroxyl or carboxylate groups such as citrate; vi) succinate; vii) tartrate; viii) lactate; ix) alkyl sulfates: Alk-O—S(O)O⁻ such as methyl sulfate and ethyl sulfate; x) aryl sulfates: Ar—O—S(O)O⁻ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphates O=P(OH)$_2$—O$^-$, O=P(O$^-$)$_2$—OH O=P(O$^-$)$_3$, HO—[P(O)(O$^-$)]$_w$—P(O)(O$^-$)$_2$ with w being an integer; xiv) acetate; xv) triflate; and xvi) borates such as tetrafluoroborate, and xvii) disulfate (O=)$_2$S(O$^-$)$_2$ or SO$_4^{2-}$ and monosulfate HSO$_4^-$.

As previously explained, the process according to the invention uses at least one thiol-comprising reducing agent, it being understood that the composition(s) containing said thiol-comprising reducing agent(s) is (are) acids, said composition(s) has (have) a pH of inclusively between 1 and 5, preferably of inclusively between 2.5 and 4.

The thiol-comprising reducing agent(s) present in the composition (A) used according to the invention are chosen from organic compounds comprising one or more mercapto (—SH or —S—) groups, or disulfide (—S—S—) groups, preferably —SH groups, and at least one other function chosen from carboxylic acid, amine, amide, ester and alcohol functions and mixtures thereof.

According to one particular embodiment of the invention, the reducing agent(s) used in the invention are chosen from those of formulae i-1 and i-2, and also the organic or mineral acid or base salts thereof, optical isomers thereof and tautomers thereof, and the solvates such as hydrates:

$$R—SH \quad \text{i-1}$$

$$R'—S—R'' \quad \text{i-2}$$

In which formulae i-1 and i-2:
R represents:
  a linear or branched (C$_1$-C$_8$) alkyl group, preferably (C$_1$-C$_6$) alkyl group,
  a) which is optionally substituted, preferably substituted, with one or more groups chosen from carboxy C(O)OH, (di)(C$_1$-C$_4$)(alkyl)amino, hydroxyl —OH and thiol —SH,
  and/or
  b) optionally interrupted with one or more heteroatoms or groups chosen from —O—, —S—, —N(R''')— wherein R''' represents a hydrogen atom or a linear or branched (C$_1$-C$_4$)alkyl group, C(O) or combinations thereof such as —O—C(O)—, —C(O)—O—, —N(R''')—C(O)— or —C(O)—N(R''')—;
  a (hetero)aryl group optionally substituted in particular with one or more hydroxyl, thiol or carboxy groups;
R' and R'', which may be identical or different, represent a (C$_1$-C$_8$)alkyl group, preferably (C$_1$-C$_6$)alkyl group, substituted with one or more groups chosen from hydroxyl, thiol and carboxy;
or else R' and R'' form, together with the sulfur atom which bears them, a heterocyclic group, comprising from 5 to 7 ring members, which is preferably saturated, which comprises from 1 to 3 heteroatoms, and which is optionally substituted (in particular with one or more (C$_1$-C$_6$)alkyl groups optionally substituted with one or more hydroxyl, thiol or carboxy groups), more preferentially the heterocyclic group is a dithiolane group optionally substituted with a (C$_1$-C$_6$)alkyl group optionally substituted with one or more carboxy groups.

According to one particular embodiment of the invention, the reducing agents are of formula i-1, in particular those for which R represents a linear or branched (C$_1$-C$_8$)alkyl group, preferably (C$_1$-C$_6$)alkyl group, substituted with one or more groups chosen from carboxy C(O)OH, amino, hydroxyl —OH, and thiol —SH;
and/or optionally interrupted with one or more heteroatoms or groups chosen from —O—, —N(R''')— wherein R''' represents a hydrogen atom or a linear or branched (C$_1$-C$_4$) alkyl group, C(O) or combinations thereof such as —O—C(O)—, —C(O)—O—, —N(R''')—C(O)— or —C(O)—N(R''')—. Preferably, R represents a linear or branched, uninterrupted (C$_1$-C$_8$)alkyl group, preferably (C$_1$-C$_6$)alkyl group.

According to another particular embodiment of the invention, the reducing agents are of formula i-1 for which R represents:
  a phenyl group optionally substituted with one or more hydroxyl, thiol or carboxy groups; or
  a heteroaryl comprising from 5 to 10 ring members, which is preferably bicyclic comprising 9 or 10 ring members, comprising from 1 to 4 heteroatoms chosen from O, S or N, preferably N, optionally substituted with one or more hydroxyl or thiol groups.

According to another particular embodiment of the invention, the reducing agents are of formula i-2, in particular those for which R' and R'', which may be identical or different, represent a (C$_1$-C$_8$)alkyl group, preferably (C$_1$-C$_6$) alkyl group, substituted with one or more groups chosen from hydroxyl, thiol and carboxy.

According to another particular embodiment of the invention, the reducing agents are of formula i-2, in particular those for which R' and R'' form, together with the sulfur atom which bears them, a heterocyclic group, comprising from 5 to 7 ring members, which is preferably saturated, which comprises from 1 to 3 heteroatoms, and which is optionally substituted with one or more (C$_1$-C$_6$)alkyl groups optionally substituted with one or more hydroxyl, thiol or carboxy groups, more preferentially the heterocyclic group is a dithiolane group optionally substituted with a (C$_1$-C$_6$) alkyl group optionally substituted with one or more hydroxyl, thiol or carboxy groups.

Preferably, the reducing agent(s) comprising at least one mercapto or disulfide group of the invention are chosen from thioglycolic acid, thiolactic acid or 2-mercaptopropionic acid, cysteine, cysteamine, homocysteine, glutathione, thioglycerol, thiomalic acid, 3-mercaptopropionic acid, thiodiglycol, 2-mercaptoethanol, dithiothreitol, thioxanthine, thiosalicylic acid, thiodiglycolic acid, lipoic acid, N-acetylcysteine, and thioglycolic or thiolactic acid esters and amides, in particular glyceryl monothioglycolate, and mixtures of these compounds.

The thiol-comprising reducing agent(s) as defined previously may be used in particular in the form of salts, in particular alkali metal salts such as sodium and potassium salts, alkaline-earth metal salts, for example magnesium and calcium salts, ammonium salts, amine salts and amino alcohol salts. Ammonium thioglycolate may thus be used as thiol.

Particularly preferably, the thiol-comprising reducing agent(s) is (are) chosen from thioglycolic acid and salts thereof, thiolactic acid and salts thereof, cysteamine and salts thereof, and mixtures thereof.

Even more preferably, the thiol-comprising reducing agent(s) is (are) chosen from thioglycolic acid and thiolactic acid.

The thiol-comprising reducing agent(s) included in the composition (A) according to the invention is (are) preferably present in an amount ranging from 0.02% to 15% by weight, preferably from 0.1% to 10%, and even more preferentially from 0.5% to 2% by weight, relative to the total weight of said composition.

The pH of the composition (A) and/or (B) according to the invention may be adjusted to the desired value by means of basifying agents or acidifying agents that are customarily used.

The organic alkaline agent(s) is (are) preferably chosen from alkanolamines, in particular mono-, di- or tri-hydroxy ($C_1$-$C_6$)alkylamine, such as triethanolamine, oxyethylenated and/or oxypropylenated ethylenediamines, amino acids, polyamines of formula (I) below, and mixtures thereof:

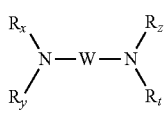

In which formula (I) W is a divalent $C_1$-$C_6$ alkylene radical optionally substituted with one or more hydroxyl groups or a $C_1$-$C_6$ alkyl radical, and/or optionally interrupted with one or more heteroatoms such as O, or —$NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (I) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$ to $C_8$ alkyl groups bearing one or more hydroxyl radicals.

Organic amines chosen from alkanolamines such as monoalkanolamines, dialkanolamines or trialkanolamines comprising one to three identical or different $C_1$ to $C_4$ hydroxyalkyl radicals are in particular suitable for performing the invention.

Among the compounds of this type, mention may be made of monoethanolamine (MEA), diethanolamine, triethanolamine, monoisopropanolamine, diisopropanolamine, N,N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethyl)aminomethane.

More particularly, the amino acids that may be used are of natural or synthetic origin, in their L, D or racemic form, and comprise at least one acid function chosen more particularly from carboxylic acid, sulfonic acid, phosphonic acid and phosphoric acid functions. The amino acids may be in neutral or ionic form.

Among the basifying agents, mention may more particularly be made of aqueous ammonia, alkanolamines, and mineral or organic hydroxides.

Among the acidifying agents, mention may be made of i) hydrochloric acid HCl, ii) hydrobromic acid HBr, iii) sulfuric acid $H_2SO_4$, iv) alkylsulfonic acids: Alk-$S(O)_2OH$, such as methanesulfonic acid and ethanesulfonic acid; v) arylsulfonic acids: Ar—$S(O)_2OH$, such as benzenesulfonic acid and toluenesulfonic acid; vi) (poly)hydroxylated carboxylic acids, such as citric acid, succinic acid, tartaric acid or lactic acid, vii) alkoxysulfinic acids: Alk-O—S(O)—OH, such as methoxysulfinic acid and ethoxysulfinic acid; viii) aryloxysulfinic acid, such as tolueneoxysulfinic acid and phenoxysulfinic acid; ix) phosphoric acid $H_3PO_4$; x) acetic acid $CH_3C(O)$—OH; xi) triflic acid $CF_3SO_3H$ and xii) tetrafluoroboric acid $HBF_4$; more particularly, the mineral or organic acids used to acidify the composition(s) are chosen from hydrochloric acid, orthophosphoric acid, sulfuric acid, carboxylic acids, for instance acetic acid, tartaric acid, citric acid and lactic acid, and sulfonic acids.

The concentration of pH-adjusting agent(s) is in particular adjusted according to the pH of 1 to 5, preferentially 2.5 to 4, designed for the composition(s) containing the thiol-comprising reducing agent(s).

According to one particular embodiment of the invention, the colouring agent(s) is (are) chosen from direct dyes.

The term "direct dye" is intended to mean natural and/or synthetic dyes, other than oxidation dyes. They are dyes that will superficially diffuse on the fibre and dye the fibres by themselves.

The direct dye(s) that can be used according to the invention are preferentially chosen from natural or synthetic direct dyes which are cationic, anionic or non-ionic.

According to one particular embodiment of the invention, the composition (B) of the process comprises a) one or more synthetic or natural direct dyes, chosen from cationic, anionic and non-ionic species, preferably cationic and non-ionic species, and more preferentially cationic species.

More particularly, the direct dye(s) a) are chosen from azo direct dyes; (poly)methine dyes such as cyanines, hemicyanines and styryls; carbonyl dyes; azine dyes; nitro(hetero) aryl dyes; tri(hetero)arylmethane dyes; porphyrin dyes; phthalocyanine dyes and natural direct dyes, alone or in the form of mixtures.

The term "natural dyes" or "dyes of natural origin" is intended to mean dyes derived from natural materials (plant, mineral or animal origin), for instance extracts, ground material and decoctions, which have a greater or smaller concentration of dyes.

Included among the natural dyes according to the invention are compounds that may be present in nature and that are reproduced by chemical (semi)synthesis.

The natural dyes may be chosen especially from spinulosin, orceins, polyphenols or ortho-diphenols (also referred to as ODPs in the rest of the description) other than the non-thiol-comprising reducing agents, and all extracts rich in ODPs, curcumin, indole derivatives such as isatin or indole-2,3-dione, indigoids including indigo, phthalocyanines and porphyrins in particular complexed to a metal, glycosyl or non-glycosyl iridoids, chromene dyes, anthraquinone and naphthoquinone dyes such as lawsone or henna, juglone, spinulosin, chromene or chroman dyes, such as neoflavanols and neoflavanones, flavanols; and anthocyanidols. Use may also be made of extracts or decoctions containing these natural dyes and especially plant extracts or poultices containing said dyes.

According to one preferred embodiment of the invention, the direct dye(s) that can be used according to the invention are chosen from anionic dyes, commonly referred to as "acid" direct dyes on account of their affinity for alkaline substances.

The term "anionic direct dye" is intended to mean any direct dye comprising in its structure at least one $CO_2R$ or $SO_3R$ substituent with R denoting a hydrogen atom or a cation originating from a metal or an amine, or an ammonium ion. The anionic dyes may be chosen from acidic nitro direct dyes, acidic azo dyes, acidic azine dyes, acidic triarylmethane dyes, acidic indoamine dyes, acidic anthraquinone dyes, indigoid dyes and acidic natural dyes.

By way of anionic (or acid) direct dyes that can be used according to the invention, mention may be made in particular of the dyes of formulae (II), (III), (IV), (V), (VI), (VII), (VIII), (IX), (X), (XI), (XII) and (XIII) below:

a) the diaryl anionic azo dyes of formula (II) or (III):

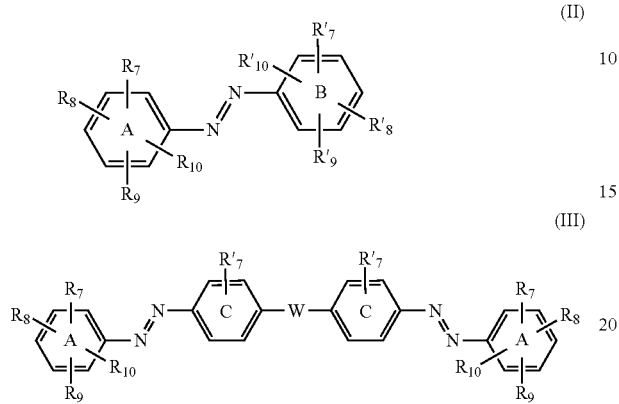

in which formulae (II) and (III):

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;

nitro, nitroso;

$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;

$(O)_2S(O^-)$—, $M^+$ with $M^+$ representing a hydrogen atom or a cationic counterion;

$(O)CO^-$—, $M^+$ with $M^+$ as defined previously;

R"—$S(O)_2$—, with R" representing a hydrogen atom or an alkyl, aryl, (di)(alkyl)amino or aryl(alkyl)amino group; preferentially a phenylamino or phenyl group;

R'"—$S(O)_2$—X'— with R'" representing an alkyl or optionally substituted aryl group, X' as defined previously;

(di)(alkyl)amino;

aryl(alkyl)amino optionally substituted with one or more groups chosen from i) nitro; ii) nitroso; iii) $(O)_2S(O^-)$—, $M^+$ and iv) alkoxy, with $M^+$ as defined previously;

optionally substituted heteroaryl; preferentially a benzothiazolyl group;

cycloalkyl; in particular cyclohexyl;

Ar—N=N— with Ar representing an optionally substituted aryl group; preferentially a phenyl optionally substituted with one or more alkyl, $(O)_2S(O—)$—, M+ or phenylamino groups;

or alternatively two contiguous groups $R_7$ with $R_8$ or $R_8$ with $R_9$ or $R_9$ with $R_{10}$ together form a fused benzo group A'; and $R'_7$ with $R'^8$ or $R'_8$ with $R'_9$ or $R'_9$ with $R'^{10}$ together form a fused benzo group B'; with A' and B' optionally substituted with one or more groups chosen from i) nitro; ii) nitroso; iii) $(O)_2S(O—)$—, M+; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N=N— and xi) optionally substituted aryl(alkyl)amino; with $M^+$, $R^o$, X, X', X" and Ar previously defined;

W represents a sigma bond 6, an oxygen or sulfur atom, or a divalent radical i) —NR— with R as defined previously, or ii) methylene —$C(R_a)(R_b)$— with $R_a$ and $R_b$, which may be identical or different, representing a hydrogen atom or an aryl group, or alternatively $R_a$ and $R_b$ form, with the carbon atom that bears them, a spiro cycloalkyl; preferentially, W represents a sulfur atom or $R_a$ and $R_b$ together form a cyclohexyl;

it being understood that formulae (II) and (III) comprise at least one sulfonate radical $(O)_2S(O^-)$—, $M^+$ or one carboxylate radical $(O)CO^-$—, $M^+$ on one of the rings A, A', B, B' or C; preferentially sodium sulfonate.

As examples of dyes of formula (II), mention may in particular be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2 and Food yellow 3 or sunset yellow.

As examples of dyes of formula (III), mention may in particular be made of: Acid Red 111, Acid Red 134 and Acid yellow 38;

b) the pyrazolone anionic azo dyes of formulae (IV) and (V):

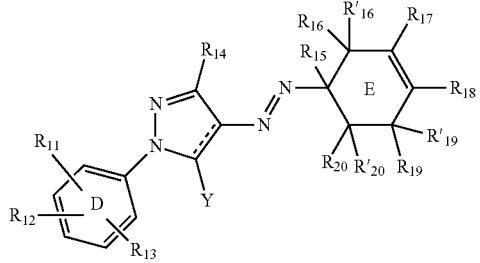

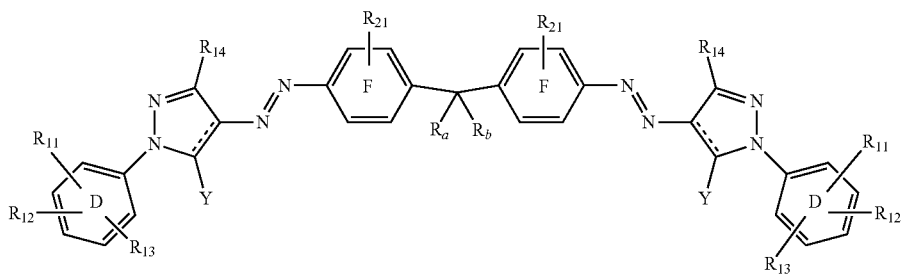

(V)

in which formulae (IV) and (V):

$R_{11}$, $R_{12}$ and $R_{13}$, which may be identical or different, represent a hydrogen or halogen atom, an alkyl group or —(O)$_2$S(O$^-$), M$^+$ with M$^+$ as defined previously;

$R_{14}$ represents a hydrogen atom, an alkyl group or a group —C(O)O—, M+ with M$^+$ as defined previously;

$R_{15}$ represents a hydrogen atom;

$R_{16}$ represents an oxo group, in which case R'$_{16}$ is absent, or alternatively $R_{15}$ with $R_{16}$ together form a double bond;

$R_{17}$ and $R_{18}$, which may be identical or different, represent a hydrogen atom, or a group chosen from:
(O)$_2$S(O$^-$)—, M$^+$ with M$^+$ as defined previously;
Ar—O—S(O)$_2$— with Ar representing an optionally substituted aryl group, preferentially a phenyl optionally substituted with one or more alkyl groups;

$R_{19}$ and $R_{20}$ together form either a double bond, or a benzo group D', which is optionally substituted;

R'$_{16}$, R'$_{19}$ and R'$_{20}$, which may be identical or different, represent a hydrogen atom or an alkyl or hydroxyl group;

$R_{21}$ represents a hydrogen atom or an alkyl or alkoxy group;

$R_a$ and $R_b$, which may be identical or different, are as defined previously, preferentially $R_a$ represents a hydrogen atom and $R_b$ represents an aryl group;

Y represents either a hydroxyl group or an oxo group;
----- represents a single bond when Y is an oxo group; and represents a double bond when Y represents a hydroxyl group;

it being understood that formulae (IV) and (V) comprise at least one sulfonate radical (O)$_2$S(O$^-$)—, M$^+$ or one carboxylate radical C(O)O$^-$—, M$^+$ on one of the rings D or E; preferentially sodium sulfonate.

As examples of dyes of formula (IV), mention may in particular be made of: Acid Red 195, Acid Yellow 23, Acid Yellow 27 and Acid Yellow 76.

As an example of a dye of formula (V), mention may be made of: Acid Yellow 17;

c) the anthraquinone dyes of formulae (VI) and (VII):

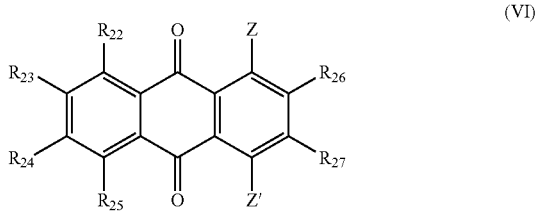

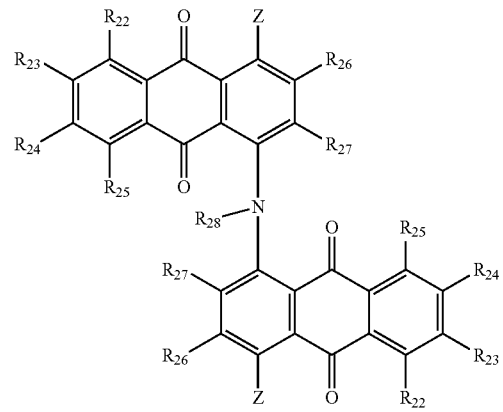

in which formulae (VI) and (VII):

$R_{22}$, $R_{23}$, $R_{24}$, $R_{25}$, $R_{26}$ and $R_{27}$, which may be identical or different, represent a hydrogen or halogen atom, or a group chosen from:
alkyl;
hydroxyl, mercapto;
alkoxy, alkylthio;
optionally substituted aryloxy or arylthio, preferentially substituted with one or more groups chosen from alkyl and (O)$_2$S(O$^-$)—, M$^+$ with M$^+$ as defined previously;
aryl(alkyl)amino optionally substituted with one or more groups chosen from alkyl and (O)$_2$S(O$^-$)—, M$^+$ with M$^+$ as defined previously;
(di)(alkyl)amino;
(di)(hydroxyalkyl)amino;
(O)$_2$S(O$^-$)—, M$^+$ with M$^+$ as defined previously;

Z' represents a hydrogen atom or a group NR$_{28}$R$_{29}$ with $R_{28}$ and $R_{29}$, which may be identical or different, representing a hydrogen atom or a group chosen from:
alkyl;
polyhydroxyalkyl such as hydroxyethyl;
aryl optionally substituted with one or more groups, more particularly i) alkyl such as methyl, n-dodecyl, n-butyl; ii) (O)$_2$S(O$^-$)—, M$^+$ with M$^+$ as defined previously; iii) R$^o$—C(X)—X'—, R$^o$—X'—C(X)—, R$^o$—X'—C(X)—X"— with R$^o$, X, X' and X" as defined previously, preferentially R$^o$ represents an alkyl group;
cycloalkyl; in particular cyclohexyl;

Z, represents a group chosen from hydroxyl and NR'$_{28}$R'$_{29}$ with R'$_{28}$ and R'$_{29}$, which may be identical or different, representing the same atoms or groups as $R_{28}$ and $R_{29}$ as defined previously;

it being understood that formulae (VI) and (VII) comprise at least one sulfonate radical $(O)_2S(O^-)$—, $M^+$ or a carboxylate radical $C(O)O^-$—, $M^+$; preferentially sodium sulfonate.

As examples of dyes of formula (VI), mention may in particular be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3 and EXT violet No 2.

As an example of a dye of formula (VII), mention may be made of: Acid Black 48;

d) the nitro dyes of formulae (VIII) and (IX):

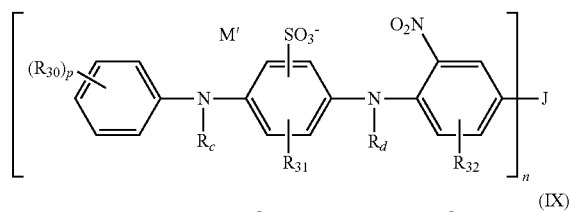

(VIII)

(IX)

in which formulae (VIII) and (IX):

$R_{30}$, $R_{31}$ and $R_{32}$, which may be identical or different, represent a hydrogen or halogen atom, or a group chosen from:
alkyl;
alkoxy optionally substituted with one or more hydroxyl groups, alkylthio optionally substituted with one or more hydroxyl groups;
hydroxyl, mercapto;
nitro, nitroso;
polyhaloalkyl;
$R^o$—C(X)—X'—, $R^o$—X'—C(X)—, $R^o$—X'—C(X)—X'— with $R^o$; X, X' and X" as defined previously;
$(O)_2S(O^-)$—, $M^+$ with $M^+$ as defined previously;
$(O)CO^-$—, $M^+$ with $M^+$ as defined previously;
(di)(alkyl)amino;
(di)(hydroxyalkyl)amino;
heterocycloalkyl such as piperidino, piperazino or morpholino;
more particularly, $R_{30}$, $R_{31}$ and $R_{32}$ represent a hydrogen atom;
$R_c$ and $R_d$, which may be identical or different, represent a hydrogen atom or an alkyl group;
W is as defined previously; W particularly represents an —NH— group;
ALK represents a linear or branched divalent $C_1$-$C_6$ alkylene group; more particularly, ALK represents a —CH$_2$—CH$_2$— group;
n is 1 or 2;
p represents an integer inclusively between 1 and 5;
q represents an integer inclusively between 1 and 4;
u is 0 or 1;

when n is 1, J represents a nitro or nitroso group; more particularly nitro;
when n is 2, J represents an oxygen or sulfur atom, or a divalent radical —S(O)$_m$— with m representing an integer 1 or 2; more preferentially, J represents a radical —SO$_2$—;
M' represents a hydrogen atom or a cationic counterion;

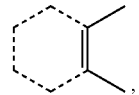

which may be present or absent, represents a benzo group optionally substituted with one or more $R_{30}$ groups as defined previously;

it being understood that formulae (VIII) and (IX) comprise at least one sulfonate radical $(O)_2S(O^-)$—, $M^+$ or a carboxylate radical $C(O)O^-$—, $M^+$; more preferentially sodium sulfonate.

As examples of dyes of formula (VIII), mention may in particular be made of: Acid Brown 13 and Acid Orange 3.

As examples of dyes of formula (IX), mention may be made of: Acid Yellow 1, the sodium salt of 2,4-dinitro-1-naphthol-7-sulfonic acid, 2-piperidino-5-nitrobenzenesulfonic acid, 2(4'-N,N(2"-hydroxyethyl)amino-2'-nitro)anilineethanesulfonic acid, 4-β-hydroxyethylamino-3-nitrobenzenesulfonic acid and EXT D&C yellow 7.

d) the triarylmethane dyes of formula (X):

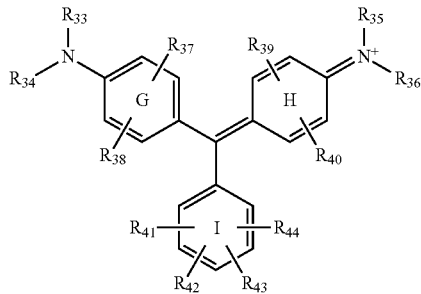

(X)

in which formula (X):
$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl and benzyl group optionally substituted with a group $(O)_mS(O^-)$—, $M^+$ with $M^+$ and m as defined previously;
$R_{37}$, $R_{38}$, $R_{39}$, $R_{40}$, $R_{41}$, $R_{42}$, $R_{43}$ and $R_{44}$, which may be identical or different, represent a hydrogen atom or group chosen from:
alkyl;
alkoxy, alkylthio;
(di)(alkyl)amino;
hydroxyl, mercapto;
nitro, nitroso;
$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;

(O)$_2$S(O$^-$)—, M$^+$ with M$^+$ representing a hydrogen atom or a cationic counterion;

(O)CO$^-$—, M$^+$ with M$^+$ as defined previously;

or alternatively two contiguous groups R$_{41}$ with R$_{42}$ or R$_{42}$ with R$_{43}$ or R$_{43}$ with R$_{44}$ together form a fused benzo group: I'; with I' optionally substituted with one or more groups chosen from i) nitro; ii) nitroso; iii) (O)$_2$S(O$^-$)—, M$^+$; iv) hydroxyl; v) mercapto; vi) (di)(alkyl)amino; vii) R$^o$—C(X)—X'—; viii) R$^o$—X'—C(X)—; ix) R$^o$—X'—C(X)—X"—; with M$^+$, R$^o$, X, X' and X" as defined previously;

more particularly, R$_{37}$ to R$_{40}$ represent a hydrogen atom, and R$_{41}$ to R$_{44}$, which may be identical or different, represent a hydroxyl group or (O)$_2$S(O$^-$)—, M$^+$; and when R$_{43}$ with R$_{44}$ together form a benzo group, it is preferentially substituted with an (O)$_2$S(O$^-$)— group;

it being understood that at least one of the rings G, H, I or I' comprises at least one sulfonate radical (O)$_2$S(O$^-$)— or a carboxylate radical —C(O)O—; more preferentially sulfonate.

As examples of dyes of formula (X), mention may in particular be made of: Acid Blue 1; Acid Blue 3; Acid Blue 7, Acid Blue 9; Acid Violet 49; Acid Green 3; Acid Green 5 and Acid Green 50.

e) the xanthene-based dyes of formula (XI):

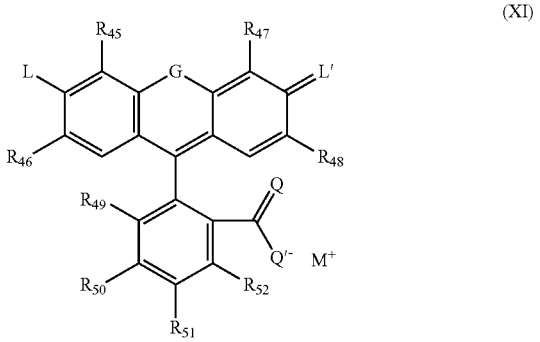

in which formula (XI):

R$_{45}$, R$_{46}$, R$_{47}$ and R$_{48}$, which may be identical or different, represent a hydrogen or halogen atom;

R$_{49}$, R$_{50}$, R$_{51}$ and R$_{52}$, which may be identical or different, represent a hydrogen or halogen atom, or a group chosen from:
alkyl;
alkoxy, alkylthio;
hydroxyl, mercapto;
nitro, nitroso;
(O)$_2$S(O$^-$)—, M$^+$ with M$^+$ representing a hydrogen atom or a cationic counterion;
(O)CO$^-$—, M$^+$ with M$^+$ as defined previously;

preferably, R$_{49}$, R$_{50}$, R$_{51}$ and R$_{52}$ represent a hydrogen or halogen atom;

G represents an oxygen or sulfur atom or a group NR$_e$ with R$_e$ as defined previously; more particularly G represents an oxygen atom;

L represents an alkoxide O$^-$, M$^+$; a thioalkoxide S$^-$, M$^+$ or a group NR$_f$, with R$_f$ representing a hydrogen atom or an alkyl group and M$^+$ as defined previously; M$^+$ is particularly sodium or potassium;

L' represents an oxygen or sulfur atom or an ammonium group: N$^+$R$_f$R$_g$, with R$_f$ and R$_g$, which may be identical or different, representing a hydrogen atom, an alkyl group or optionally substituted aryl; L' represents more particularly an oxygen atom or a phenylamino group optionally substituted with one or more alkyl or (O)$_m$S(O$^-$)—, M$^+$ groups with m and M$^+$ as defined previously;

Q and Q', which may be identical or different, represent an oxygen or sulfur atom; more particularly Q and Q' represent an oxygen atom;

M$^+$ is as defined previously;

As examples of dyes of formula (X), mention may in particular be made of: Acid Yellow 73; Acid Red 51; Acid Red 52; Acid Red 87; Acid Red 92; Acid Red 95 and Acid Violet 9;

f) the indole-based dyes of formula (XII):

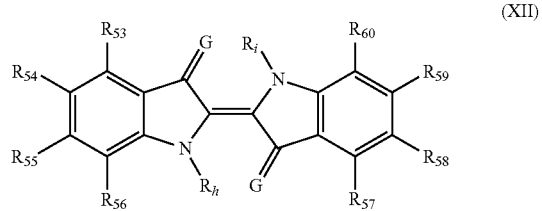

in which formula (XII):

R$_{53}$, R$_{54}$, R$_{55}$, R$_{56}$, R$_{57}$, R$_{58}$, R$_{59}$ and R$_{60}$, which may be identical or different, represent a hydrogen atom or group chosen from:
alkyl;
alkoxy, alkylthio;
hydroxyl, mercapto;
nitro, nitroso;
R$^o$—C(X)—X'—, R$^o$—X'—C(X)—, R$^o$—X'—C(X)—X"— with R$^o$ representing a hydrogen atom or an alkyl or aryl group; X, X' and X", which may be identical or different, representing an oxygen or sulfur atom, or NR with R representing a hydrogen atom or an alkyl group;
(O)$_2$S(O$^-$)—, M$^+$ with M$^+$ representing a hydrogen atom or a cationic counterion;
(O)CO$^-$—, M$^+$ with M$^+$ as defined previously;
G represents an oxygen or sulfur atom or a group NR$_e$ with R$_e$ as defined previously; more particularly G represents an oxygen atom;
R$_i$ and R$_h$, which may be identical or different, represent a hydrogen atom or an alkyl group;

it being understood that formula (XII) comprises at least one sulfonate radical (O)$_2$S(O$^-$)—, M$^+$ or a carboxylate radical —C(O)O—, M$^+$; more preferentially sodium sulfonate;

As an example of a dye of formula (XII), mention may in particular be made of: Acid Blue 74;

g) the quinoline-based dyes of formula (XIII):

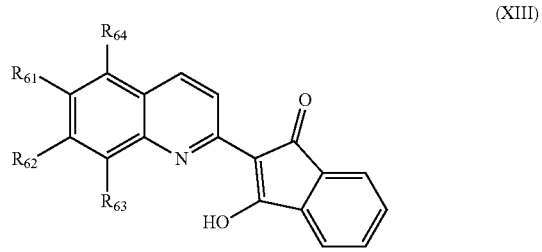

$R_{61}$ represents a hydrogen or halogen atom or an alkyl group;

$R_{62}$, $R_{63}$, and $R_{64}$, which may be identical or different, represent a hydrogen atom or a group $(O)_2S(O^-)$—, $M^+$ with $M^+$ representing a hydrogen atom or a cationic counterion;

or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (XIII) comprises at least one sulfonate radical $(O)_2S(O^-)$—, more preferentially sodium sulfonate.

As examples of dyes of formula (XIII), mention may in particular be made of: Acid Yellow 2, Acid Yellow 3 and Acid Yellow 5.

The direct dye(s) that can be used according to the invention are preferentially chosen from those of formulae (II), (III), (IV), (V), (VI), (VII), (VIII), (IX), (X), (XI), (XII) and (XIII) as defined above.

More particularly, the dyes of formulae (II) to (XIII) that can be used according to the invention are chosen from:

| | |
|---|---|
| (C.I. 45380) | Acid Red 87 (formula XI) |
| (C.I. 10316) | Sodium salt of of 2,4-dinitro-1-naphthol-7-sulfonic acid (formula IX) |
| (C.I. 10383) | Acid Orange 3 (formula VIII) |
| (C.I. 13015) | Acid Yellow 9/Food Yellow 2 (formula II) |
| (C.I. 14780) | Direct Red 45/Food Red 13 (formula II) |
| (C.I. 13711) | Acid Black 52 (formula II) |
| (C.I. 13065) | Acid Yellow 36 (formula II) |
| (C.I. 14700) | Sodium salt of 1-hydroxy-2-(2',4'-xylyl-5-sulfonatoazo)naphthalene-4-sulfonic acid/Food Red 1 (formula II) |
| (C.I. 14720) | Acid Red 14/Food Red 3/Mordant Blue 79 (formula II) |
| (C.I. 14805) | Sodium salt of 4-hydroxy-3-[(2-methoxy-5-nitrophenyl)diaza]-6-(phenylamino)naphthalene-2-sulfonic acid/Acid Brown 4 (formula II) |
| (C.I. 15510) | Acid Orange 7/Pigment Orange 17/Solvent Orange 4 (formula II) |
| (C.I. 15985) | Food Yellow 3/Pigment Yellow 104 (formula II) |
| (C.I. 16185) | Acid Red 27/Food Red 9 (formula II) |
| (C.I. 16230) | Acid Orange 10/Food Orange 4 (formula II) |
| (C.I. 16250) | Acid Red 44 (formula II) |
| (C.I. 17200) | Acid Red 33/Food Red 12 (formula II) |
| (C.I. 15685) | Acid Red 184 (formula II) |
| (C.I. 19125) | Acid Violet 3 (formula II) |
| (C.I. 18055) | Sodium salt of 1-hydroxy-2-(4'-acetamidophenylazo)-8-acetamidonaphthalene-3,6-disulfonic acid/Acid Violet 7/Food Red 11 (formula II) |
| (C.I. 18130) | Acid Red 135 (formula II) |
| (C.I. 19130) | Acid Yellow 27 (formula IV) |
| (C.I. 19140) | Acid Yellow 23/Food Yellow 4 (formula IV) |
| (C.I. 20170) | 4'-(sulfonato-2'',4''-dimethyl)bis(2,6-phenylazo)-1,3-dihydroxybenzene/Acid Orange 24 (formula II) |
| (C.I. 20470) | Sodium salt of 1-amino-2-(4'-nitrophenylazo)-7-phenylazo-8-hydroxynaphthalene-3,6-disulfonic acid/Acid Black 1 (formula II) |
| (C.I. 23266) | (4-((4-methylphenyl)sulfonyloxy)phenylazo)-2,2'-dimethyl-4-((2-hydroxy-5,8-disulfonato)naphthylazo)biphenyl/Acid Red 111 (formula III) |
| (C.I. 27755) | Food Black 2 (formula II) |
| (C.I. 25440) | 1-(4'-sulfonatophenylazo)-4-((2''-hydroxy-3''-acetylamino-6'',8''-disulfonato)naphthylazo)-6-sulfonatonaphthalene (tetrasodium salt)/Food Black 1 (formula II) |
| (C.I. 42090) | Acid Blue 9 (formula X) |
| (C.I. 60730) | Acid Violet 43 (formula VI) |
| (C.I. 61570) | Acid Green 25 (formula VI) |
| (C.I. 62045) | Sodium salt of 1-amino-4-cyclohexylamino-9,10-anthraquinone-2-sulfonic acid/Acid Blue 62 (formula VI) |
| (C.I. 62105) | Acid Blue 78 (formula VI) |
| (C.I. 14710) | Sodium salt of 4-hydroxy-3-((2-methoxyphenyl)azo)-1-naphthalenesulfonic acid/Acid Red 4 (formula II) 2-Piperidino-5-nitrobenzenesulfonic acid (formula IX) 2-(4'-N,N-(2''-Hydroxyethyl)amino-2'-nitro)anilineethanesulfonic acid (formula IX) 4-β-Hydroxyethylamino-3-nitrobenzenesulfonic acid (formula IX) |
| (C.I. 42640) | Acid Violet 49 (formula X) |
| (C.I. 42080) | Acid Blue 7 (formula X) |
| (C.I. 58005) | Sodium salt of 1,2-dihydroxy-3-sulfoanthraquinone/Mordant Red 3 (VI) |
| (C.I. 62055) | Sodium salt of 1-amino-9,10-dihydro-9,10-dioxo-4-(phenylamino) 2-anthracenesulfonic acid/Acid Blue 25 (formula VI) |
| (C.I. 14710) | Sodium salt of 4-hydroxy-3-((2-methoxyphenyl)azo)-1-naphthalenesulfonic acid/Acid Red 4 (formula II) |

Most of these dyes are described in particular in the *Colour Index* published by The Society of Dyers and Colourists, P.O. Box 244, Perkin House, 82 Grattan Road, Bradford, Yorkshire, BD12 JBN England.

The anionic direct dye(s) that are particularly preferred according to the invention are chosen from the compounds of formulae (II) and (III).

It is also possible to use compounds corresponding to the mesomeric or tautomeric forms of structures (II) to (XIII).

According to one preferred embodiment of the invention, the direct dye(s) that can be used according to the invention are chosen from anionic direct dyes; preferably from anionic direct azo dyes, such as the diaryl anionic azo dyes of formulae (II) or (III) as defined above; more preferably from anionic direct azo dyes of formula (II) such as the acid Red 18.

According to another particular embodiment, the dye(s) of the invention are chosen from cationic direct dyes. The term "cationic direct dye" is intended to mean dyes of which the chromophore(s) is (are) cationic, i.e. comprising a quaternized heteroatom such as ammonium or at least one chromophore bearing a cationic group comprising a quaternized heteroatom such as ammonium.

According to one specific embodiment of the invention, the cationic direct dyes comprise at least one quaternized cationic chromophore.

Mention may be made, as cationic direct dyes according to the invention, of the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, in particular nitro(hetero)aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones;

squaranes; tetrazoliums; thiazines; thioindigos; thiopyronines; triarylmethanes or xanthenes.

Mention may in particular be made, for the cationic azo dyes, of those resulting from the cationic dyes described in the Kirk-Othmer Encyclopedia of Chemical Technology, "Dyes, Azo", J. Wiley & Sons, updated on 19 Apr. 2010.

According to one embodiment, the cationic direct dyes are chosen from those comprising an exocyclic cationic charge.

When the cationic charge is exocyclic, it is for example an ammonium or phosphonium substituent $R^+$, such as trimethylammonium, which is:

either outside the heteroaryl, such as pyridinyl, indolyl, imidazolyl or naphthalimidyl in question:

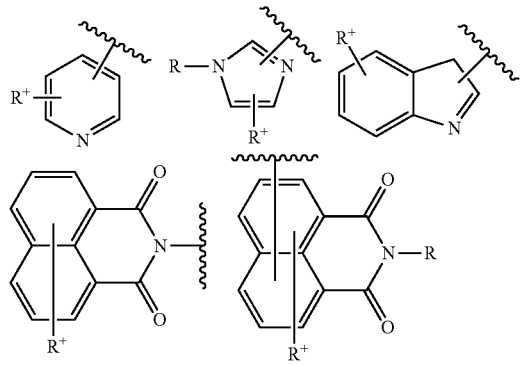

with R a heteroaryl substituent as defined above and $R^+$ an ammonium $R_aR_bR_cN^+$—, phosphonium $R_aR_bR_cP^+$— or ammonium $R_aR_bR_cN^+$—$(C_1-C_6)$alkylamino group with $R_a$, $R_b$ and $R_c$, which are identical or different, representing a hydrogen atom or a $(C_1-C_8)$alkyl group, such as methyl;

or outside the aryl, i.e. the quaternized cationic group is outside said ring, it is in particular an ammonium or phosphonium substituent $R^+$, such as trimethylammonium, which is outside the aryl, such as phenyl or naphthyl:

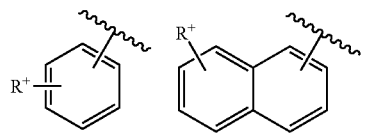

Among the azo dyes that may be used according to the invention, mention may be made of the cationic azo dyes described in patent applications WO 95/15144, WO 95/01772 and EP-714954.

According to a preferred embodiment of the invention, the direct dye(s) are chosen from cationic dyes known as "basic dyes".

Mention may be made, among the azo dyes described in the Colour Index International, 3rd edition, in particular of the following compounds:
Basic Red 22
Basic Red 76
Basic Yellow 57
Basic Brown 16
Basic Brown 17.

Among the cationic quinone dyes, those mentioned in the abovementioned Colour Index International are suitable and, among these, mention may be made, inter alia, of the following dyes:
Basic Blue 22
Basic Blue 99.

Among the azine dyes which are suitable, mention may be made of those listed in the Colour Index International, for example of the following dyes:
Basic Blue 17.
Basic Red 2.

Among the cationic triarylmethane dyes which may be used according to the invention, mention may be made, in addition to those listed in the Colour Index, of the following dyes:
Basic Green 1
Basic Violet 3
Basic Violet 14
Basic Blue 7.
Basic Blue 26.

Mention may also be made of the cationic dyes described in the documents U.S. Pat. No. 5,888,252, EP 1 133 975, WO 03/029 359, EP 860 636, WO 95/01772, WO 95/15144 and EP 714 954. Mention may also be made of those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

Preferably, the cationic direct dyes are chosen from those resulting from dyes of azo and hydrazono type.

According to a specific embodiment, the direct dyes are cationic azo dyes, described in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4 220 388, DE 4 137 005, WO 01/66646, U.S. Pat. No. 5,708,151, WO 95/01772, WO 515 144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the cationic direct dye(s) comprise a quaternary ammonium group; more preferentially, the cationic charge is endocyclic.

When the cationic charge is endocyclic, it is included in the electron delocalization via the mesomeric effect of the heteroaryl bearing the charge, for example it is a pyridinium, imidazolium or indolinium group:

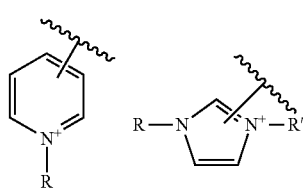

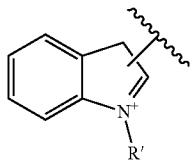

with R and R' being a heteroaryl substituent as defined above and particularly a (hydroxy)($C_1$-$C_8$)alkyl group such as methyl;

These cationic radicals are, for example, a cationic radical:

- bearing an exocyclic (di/tri)($C_1$-$C_8$)alkylammonium charge, or
- bearing an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, phenazinium, phenooxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention being be made of the hydrazono cationic dyes of formulae (XXII) and (XXIII), the azo dyes of formulae (XXIV) and (XXV) below, and also the optical and geometric isomers thereof and tautomers thereof, the organic or mineral acids or bases thereof, and also the solvates thereof such as hydrates:

$$\text{Het}^+\text{-C}(R_a)\text{=N—N}(R_b)\text{—Ar,Q}^- \qquad (XXII)$$

$$\text{Het}^+\text{-N}(R_a)\text{—N=C}(R_b)\text{—Ar,Q}^- \qquad (XXIII)$$

$$\text{Het}^+\text{-N=N—Ar,Q}^- \qquad (XXIV)$$

$$\text{Ar}^+\text{—N=N—Ar'',Q}^- \qquad (XXV)$$

in which formulae (XXII) to (XXV):

Het$^+$ represents a cationic heteroaryl radical, preferentially bearing an endocyclic cationic charge, such as imidazolium, indolium or pyridinium, optionally substituted, preferentially with at least one ($C_1$-$C_8$) alkyl group such as methyl;

Ar$^+$ represents an aryl radical, such as phenyl or naphthyl, having an exocyclic cationic charge, preferentially ammonium, particularly tri($C_1$-$C_8$)alkylammonium, such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar'' represents an optionally substituted (hetero)aryl group, such as phenyl or pyrazolyl, which are optionally substituted, preferentially by one or more ($C_1$-$C_8$) alkyl, hydroxyl, (di)($C_1$-$C_8$)(alkyl)amino, ($C_1$-$C_8$) alkoxy or phenyl groups;

$R_a$ and $R_b$, which may be identical or different, represent a hydrogen atom or a ($C_1$-$C_8$)alkyl group, which is optionally substituted, preferentially with a hydroxyl group;

or else the $R_a$ substituent with a substituent of Het$^+$ and/or $R_b$ with a substituent of Ar form, together with the atoms that bear them, a (hetero)cycloalkyl; in particular, $R_a$ and $R_b$ represent a hydrogen atom or a ($C_1$-$C_4$) alkyl group optionally substituted with a hydroxyl group;

Q$^-$ represents an organic or mineral anionic counterion, such as a halide or an alkyl sulfate.

In particular, mention may be made of the azo and hydrazono direct dyes bearing endocyclic cationic charges, of formulae (XXII) to (XXV) as defined previously, more particularly cationic direct dyes of formulae (XXII) to (XXV) bearing endocyclic cationic charges described in patent applications WO 95/15144, WO 95/01772 and EP-714954.

Preferentially, mention may be made of the following direct dyes:

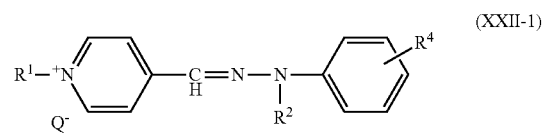

(XXII-1)

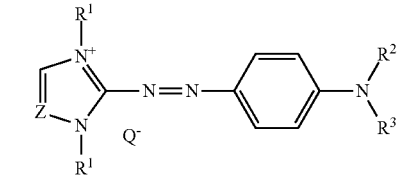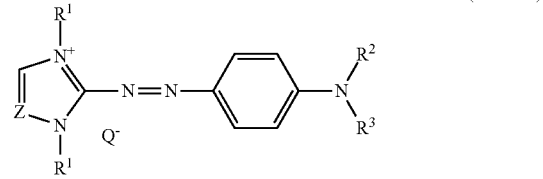

(XXIV-1)

in which formulae (XXII-1) and (XXIV-1):

$R^1$ represents a ($C_1$-$C_4$)alkyl group such as methyl;

$R^2$ and $R^3$, which may be identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom, Z represents a CH group or a nitrogen atom, preferentially CH, Q$^-$ is an anionic counterion as defined above, in particular a halide, such as chloride, or an alkyl sulfate, such as methyl sulfate or mesityl.

Particularly, the dyes of formulae (XXII-1) and (XXIV-1) are chosen from Basic Red 51, Basic Yellow 87 and Basic Orange 31 or derivatives thereof:

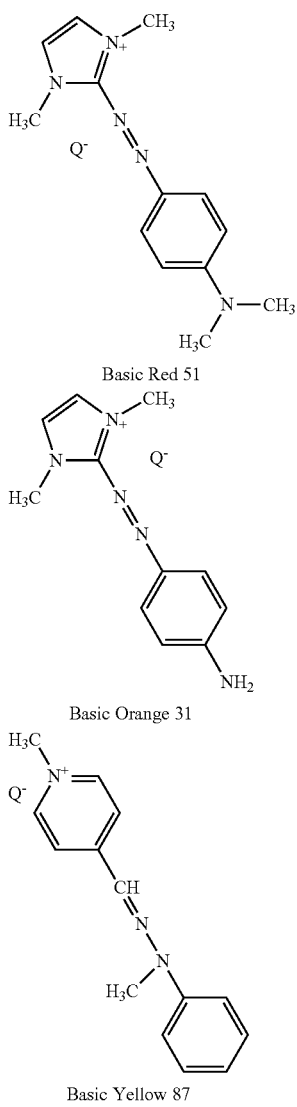

Basic Red 51

Basic Orange 31

Basic Yellow 87 with Q' being an anionic counterion as defined above, in particular a halide, such as chloride, or an alkyl sulfate, such as methyl sulfate or mesityl.

According to a specific embodiment of the invention, the direct dyes are fluorescent, that is to say that they contain at least one fluorescent chromophore as defined previously.

Mention may be made, as fluorescent dyes, of the radicals resulting from the following dyes: acridines, acridones, benzanthrones, benzimidazoles, benzimidazolones, benzindoles, benzoxazoles, benzopyrans, benzothiazoles, coumarins, difluoro {2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamines (such as dansyls), oxadiazoles, oxazines, perilones, perinones, perylenes, polyenes/carotenoids, squaranes, stilbenes and xanthenes.

Mention may also be made of the fluorescent dyes described in the documents EP 1 133 975, WO 03/029 359, EP 860 636, WO 95/01772, WO 95/15144 and EP 714 954 and those listed in the encyclopaedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons, and in the handbook—"A Guide to Fluorescent Probes and Labeling Technologies", 10th Ed., Molecular Probes/Invitrogen—Oregon 2005, circulated on the Internet or in the preceding printed editions.

According to one preferred variant of the invention, the cationic dye(s) comprise at least one cationic polymethine chromophore of formula (V1) or (V2) below, and also the optical and geometric isomers thereof, the tautomers thereof, the organic or mineral acid or base salts thereof, and also the solvates thereof such as hydrates:

$$W^+ \text{—}[C(R_c)\text{=}C(R_d)]_{m'}\text{—}Ar\text{—}*,Q^- \quad (V1) \text{ or}$$

$$*\text{—}W^+ \text{—}[C(R_c)\text{=}C(R_d)]_{m'}\text{—}Ar,Q^- \quad (V2)$$

in which formula (V1) or V2):

$W^+$ represents a cationic heterocyclic or heteroaryl group, particularly comprising a quaternary ammonium optionally substituted by one or more $(C_1\text{-}C_8)$alkyl groups, optionally substituted especially by one or more hydroxyl groups;

Ar representing an aryl group such as phenyl or naphthyl, optionally substituted preferentially with i) one or more halogen atoms such as chlorine or fluorine; ii) one or more groups $(C_1\text{-}C_8)$alkyl, preferably of $C_1\text{-}C_4$ such as methyl; iii) one or more hydroxyl groups; iv) one or more $(C_1\text{-}C_8)$alkoxy groups such as methoxy; v) one or more hydroxy$(C_1\text{-}C_8)$alkyl groups such as hydroxyethyl, vi) one or more amino groups or $(di)(C_1\text{-}C_8)$alkylamino, preferably with the $C_1\text{-}C_4$ alkyl part optionally substituted with one or more hydroxyl groups, such as (di)hydroxyethylamino, vii) with one or more acylamino groups; viii) one or more heterocycloalkyl groups such as piperazinyl, piperidyl or 5- or 6-membered heteroaryl such as pyrrolidinyl, pyridyl and imidazolinyl;

m' represents an integer between 1 and 4 inclusive, and in particular m is 1 or 2; more preferentially 1;

$R_c$ and $R_d$, which are identical or different, represent a hydrogen atom or an optionally substituted $(C_1\text{-}C8)$ alkyl group, preferentially of $C_1\text{-}C4$, or alternatively $R_c$ contiguous with $W^+$ and/or $R_d$ contiguous with Ar form, with the atoms that carry them, a (hetero)cycloalkyl; particularly, $R_c$ is contiguous with $W^+$ and they form a (hetero)cycloalkyl such as cyclohexyl;

$Q^-$ is an organic or mineral anionic counterion as defined previously;

* represents the point of anchorage of the chromophore to the rest of the molecule.

According to one preferred embodiment of the invention, the dye(s) is (are) cationic mono- or dichromophore dyes having the formulae below:

$$A\text{-}(X)_p\text{—}C_{sat}\text{—}H \quad (XXVI)$$

$$A\text{-}(X)_p\text{—}C_{sat}\text{—}(X')_{p'}\text{-}A' \quad (XXVI')$$

the organic or mineral acid salts, optical isomers and geometric isomers thereof, and the solvates such as hydrates;

in which formula (XXVI) or (XXVI'):

A, and A', which may be identical or different, represent a chromophore which is preferably fluorescent and cationic or non-cationic;

X and X', which may be identical or different, represent a linear or branched, saturated or unsaturated $C_1\text{-}C_{30}$ hydrocarbon-based chain, optionally interrupted and/or optionally terminated at one or both of its ends with one or more divalent groups or heteroatoms or combinations thereof chosen from:

—N(R)—, —N$^{30}$(R)(R)—, —O—, —S—, —C(O)—, —SO$_2$— with R, which may be identical or different, chosen from a hydrogen and a $C_1$-$C_4$ alkyl, hydroxyalkyl or aminoalkyl radical;

the indices p and p', which may be identical or different, are equal to 0 or 1;

$C_{sat}$, represents a linear or branched $C_1$-$C_{18}$ alkylene chain, optionally substituted, and/or optionally interrupted with one or more divalent groups or heteroatoms or combinations thereof chosen from:

—N(R)—, —N$^+$(R)(R)—, —O—, —S—, —C(O)—, —SO$_2$— with R, which may be identical or different, chosen from a hydrogen and a $C_1$-$C_4$ alkyl, hydroxyalkyl or aminoalkyl radical.

Preferably, the dye(s) of formula (XXVI) are such that A or A' are identical or different and contain a cationic polymethine chromophore, more particularly chosen from V1 and V2, preferably V2.

More particularly, A and A', which may be identical or different, more preferentially identical, represent W—C(R$^c$)=C(R$^d$)—Ar—* or *—W—C(R)=C(R$^d$)—Ar, preferably *—W—C(R$^c$)=C(R$^d$)—Ar, with W representing a heterocycle or a heteroaryl, comprising a quaternary ammonium; Ar represents a 5- or 6-membered (hetero)aryl radical of phenyl or pyridium type, or a (hetero)aromatic bicycle of naphthyl, benzopyridnium, indolinyl or benzoindolinyl type optionally substituted with one or more halogen atoms; with one or more alkyl groups; with one or more hydroxyl groups; with one or more alkoxy groups, with one or more hydroxyalkyl groups, with one or more amino or (di)alkylamino groups, with one or more acylamino groups; with one or more 5- or 6-membered heterocycloalkyl or heteroaryl groups; R and R$^d$, which may be identical or different, represent a hydrogen atom or a $C_1$-$C_4$ alkyl group. More preferentially, W represents an imidazolium, pyridinium, benzopyridinium, benzimidazolium, quinolinium or pyrazolium.

Preferably, the dye(s) are chosen from the dyes of formula (XXVII)

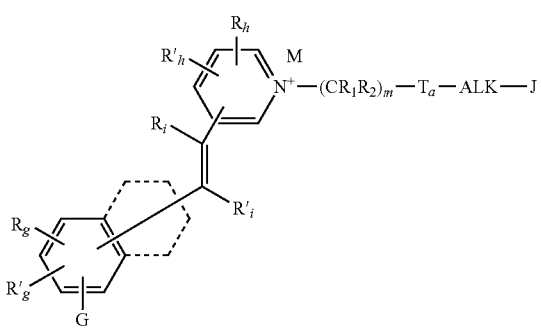

in which compound of formula (XXVII):

J represents a hydrogen atom or the group (XXVIIa) below:

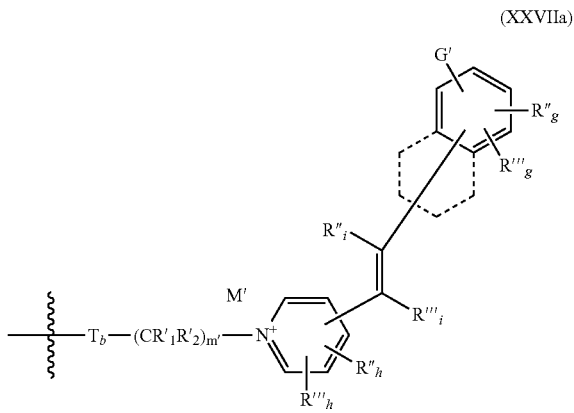

(XXVIIa)

G and G', which may be identical or different, represent an —NR$_c$R$_d$ or —NR'$_c$R'$_d$ group, or a ($C_1$-$C_6$)alkoxy group, preferably a di(hydroxy)($C_1$-$C_4$)alkylamino group;

ALK represents a ($C_1$-$C_6$)alkylene chain optionally interrupted with one or more divalent heteroatoms or groups or combinations thereof chosen from —N(R)—, —O—, —S— and —C(O)—, with R, which may be identical or different, chosen from a hydrogen and a $C_1$-$C_4$, alkyl radical;

$R_g$, $R'_g$, $R''_g$, $R'''_g$, $R_h$, $R'_h$, $R''_h$, and $R'''_h$, which may be identical or different, represent a hydrogen atom, a halogen atom, an amino, $C_1$-$C_4$ alkylamino, $C_1$-$C_4$ dialkylamino, carboxy or hydroxyl group, or a $C_1$-$C_4$ alkyl radical optionally substituted with a group chosen from $C_1$-$C_4$ alkoxy and hydroxy;

or else two groups $R_g$ and $R'_g$; $R''_g$ and $R'''_g$; $R_h$, and $R'_h$; $R''_h$ et $R'''_h$, borne by two adjacent carbon atoms, together form a benzo or indeno ring, or a fused heterocycloalkyl or fused heteroaryl group; or else G represents —NR$_c$R$_d$ and G' represents —NR'$_c$R'$_d$ and two groups R, and R'$_g$; R'$_c$ and R''$_g$; R$_d$ and R$_g$; R'$_d$ and R'''$_g$ together form a saturated heteroaryl or heterocycle, optionally substituted with a $C_1$-$C_6$ alkyl group; preferably, R'$_g$; R'$_c$ and R''$_g$; R$_d$ and R$_g$; R'$_d$ and R'''$_g$ represent a hydrogen atom;

$R_i$, $R'_i$, $R''_i$, and $R'''_i$, which may be identical or different, represent a hydrogen atom or a $C_1$-$C_4$ alkyl group;

$R_1$, $R_2$, $R_3$, $R_4$, $R'_1$, $R'_2$, $R'_3$ and $R'_4$, which may be identical or different, represent a hydrogen atom or a group ($C_1$-$C_4$)alkyl;

$T_a$ and $T_b$, which may be identical or different, represent i) either a covalent σ bond, ii) or one or more radicals or combinations thereof chosen from —SO$_2$—, —O—, —S—, —N(R)—, —N$^+$(R)(R$^o$)— and —CO—, with R and R$^o$, which may be identical or different, representing a hydrogen atom, a $C_1$-$C_4$ alkyl or $C_1$-$C_4$ hydroxyalkyl radical; or an aryl($C_1$-$C_4$)alkyl, preferably $T_a$ and $T_b$ represent a covalent bond;

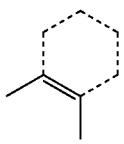

represent an aryl or heteroaryl group which is fused to the phenyl ring; or else is absent from the phenyl ring; preferably absent;

m and m', which may be identical different, represent an integer between 1 and 6 inclusive;

M' representing an anionic counterion or an organic or mineral acid salt.

More preferentially chosen from the dyes of formula (XXVIII) below:

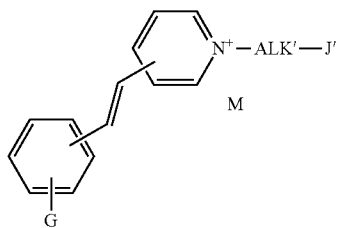

in which compound of formula (XXVIII):

J' represents a hydrogen atom or the group (VIIIa) below:

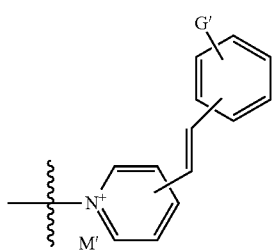

(VIIIa)

G and G', which may be identical or different, represent an —$NR_cR_d$ or —$NR'_cR'_d$ group, or a ($C_1$-$C_6$)alkoxy group, preferably a di(hydroxy)($C_1$-$C_4$)alkylamino group;

ALK' represents a ($C_1$-$C_{10}$)alkylene, preferably ($C_1$-$C_6$) alkylene, chain which is uninterrupted or interrupted with one or more divalent groups or heteroatoms or combinations thereof chosen from —N(R)—, —O—, —S— and —C(O)—, with R, which may be identical or different, chosen from a hydrogen and a $C_1$-$C_4$ alkyl radical.

According to one particular embodiment, the dye(s) of the invention is (are) chosen from non-ionic direct dyes, i.e. dyes bearing neither a positive charge nor a negative charge.

In particular, the non-ionic dye(s) is (are) chosen from nitrobenzene dyes.

The nitrobenzene direct dye(s) in accordance with the invention are preferably chosen from the compounds of formula (XXIX) below:

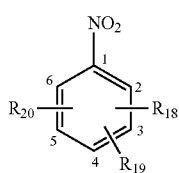

(XXIX)

in which formula (XXIX):

$R_{18}$ represents an amino radical; an amino radical monosubstituted or disubstituted with a $C_1$-$C_4$ alkyl, $C_1$-$C_4$ monohydroxyalkyl, $C_2$-$C_4$ polyhydroxyalkyl, $C_1$-$C_4$ aminoalkyl, mono($C_1$-$C_4$)alkylamino($C_1$-$C_4$)alkyl, di($C_1$-$C_4$)alkylamino($C_1$-$C_4$)alkyl, $C_1$-$C_4$ ureidoalkyl, aryl radical, in which aryl radical the aryl ring is substituted with one or more hydroxyl, carboxyl, amino or di($C_1$-$C_4$)alkylamino radicals, preferably $R_{18}$ represents a (di)($C_1$-$C_4$)(alkyl)amino group; preferably, $R_{18}$ is in position 2 or 4;

$R_{19}$ represents a hydrogen atom; an amino radical; a hydroxyl radical; a $C_1$-$C_4$ alkyl radical; a $C_1$-$C_4$ alkoxy radical; a $C_1$-$C_4$ monohydroxyalkyl radical; a $C_2$-$C_4$ polyhydroxyalkyl radical; a $C_1$-$C_4$ monohydroxyalcoxy radical; a $C_2$-$C_4$ polyhydroxyalcoxy radical; a $C_1$-$C_4$ aminoalkoxy radical; an amino radical monosubstituted or disubstituted with a $C_1$-$C_4$ alkyl, $C_1$-$C_4$ monohydroxyalkyl, $C_2$-$C_4$ polyhydroxyalkyl, $C_1$-$C_4$ aminoalkyl, mono($C_1$-$C_4$)alkylamino($C_1$-$C_4$)alkyl, di($C_1$-$C_4$)alkylamino($C_1$-$C_4$)alkyl, $C_1$-$C_4$ ureidoalkyl, or aryl radical, in which aryl radical the aryl ring is substituted with one or more hydroxyl, carboxyl, amino or di($C_1$-$C_4$)alkylamino radicals; preferably, $R_{19}$ represents a hydrogen atom or a hydroxy or (di)($C_1$-$C_4$)(alkyl)amino group; preferably, $R_{19}$ is in position 4 or 6;

$R_{20}$ represents a hydrogen or halogen atom, a $C_1$-$C_4$ alkyl radical or a nitro group; preferably, $R_{20}$ represents a hydrogen atom.

Among the nitrobenzene dyes of formula (XXIX) above, mention may most particularly be made of:

4-amino-3-nitrophenol or 2-amino 5-hydroxynitrobenzene,
2-amino-4-methyl-5-N-(β-hydroxyethyl)aminonitrobenzene,
4-N-(β-ureidoethyl)aminonitrobenzene,
4-(N-ethyl N-β-hydroxyethyl)amino-1-N-(β-hydroxyethyl) aminonitrobenzene,
2-N-(β-hydroxyethyl)amino-5-methylnitrobenzene,
5-chloro 3-N-(ethyl)amino-4-hydroxynitrobenzene,
le 5-amino-3-chloro 4-hydroxynitrobenzene,
2-N-(γ-hydroxypropyl)amino-5-N,N-bis(β-hydroxyethyl) aminonitrobenzene,
5-hydroxy-2-N-(γ-hydroxypropyl)aminonitrobenzene,
1,3-bis-(β-hydroxyethyl)amino-4-chloro-6-nitrobenzene,
2,4-diaminonitrobenzene,
3,4-diaminonitrobenzene,
2,5-diaminonitrobenzene,
3-amino-4-hydroxynitrobenzene,
4-amino-3-hydroxynitrobenzene,
5-amino-2-hydroxynitrobenzene,
4-amino-3-hydroxynitrobenzene,
5-amino-2-hydroxynitrobenzene,
2-amino-3-hydroxynitrobenzene,
2-amino-5-N-(β-hydroxyethyl)aminonitrobenzene,
2-amino-5-N,N-bis-(β-hydroxyethyl)aminonitrobenzene,
2,5-N,N'-(β-hydroxyethyl)aminonitrobenzene,
2-N-(β-hydroxyethyl)amino-5-N,N-bis(β-hydroxyethyl) aminonitrobenzene,
2-amino-5-N-(–methyl)aminonitrobenzene,
2-N-(methyl)amino-5-N,N-bis(β-hydroxyethyl)aminonitrobenzene,
2-N-(methyl)amino-5-(N-methyl N-β-hydroxyethyl)aminonitrobenzene,
2,5-N,N'-(β-hydroxyethyl)aminonitrobenzene,
2-N-(β-hydroxyethyl)amino-5-hydroxynitrobenzene,
3-methoxy 4-N-(β-hydroxyethyl)aminonitrobenzene,
2-N-(methyl)amino-4-β-hydroxyethyloxynitrobenzene,
2-amino 3-methylnitrobenzene,
2-N-(β-hydroxyethyl)amino-5-aminonitrobenzene, 2-amino-4-chloro-5-N-(β-hydroxyethyl)aminonitrobenzene,
2-amino-4-methyl-5-N-(β-hydroxyethyl)aminonitrobenzene,
2-amino-4-methyl-5-N-(methyl)aminonitrobenzene,
2-N-(β-hydroxyethyl)amino-5-methoxynitrobenzene,
2-amino 5-β-hydroxyethyloxynitrobenzene,
2-N-(β-hydroxyethyl)aminonitrobenzene,
3-amino-4-N-(β-hydroxyethyl)aminonitrobenzene,
3-β-hydroxyethyloxy-4-N-(β-hydroxyethyl)aminonitrobenzene,
2-N-(methyl)amino-4-β,γ-dihydroxypropyloxynitrobenzene,
2-N-(β-hydroxyethyl)amino-5-β-hydroxyethyloxynitrobenzene,
2-N-(β-hydroxyethyl)amino-5-β,γ-dihydroxypropyloxynitrobenzene,
2-hydroxy 4-N-(β-hydroxyethyl)aminonitrobenzene,
2-N-(methyl)amino-4-methyl-5-aminonitrobenzene,
2-amino-4-isopropyl-5-N-(methyl)aminonitrobenzene,
2-N-(methyl)amino 5-(N-methyl-N-β,γ-dihydroxypropyl)aminonitrobenzene,
3-N-(β-hydroxyethyl)amino-4-N-(β-hydroxyethyl)aminonitrobenzene,
2-amino-4-methyl-5-N-(γ-dihydroxypropyl)aminonitrobenzene,
2-amino-4-methyl-5-hydroxynitrobenzene,
2-N-(β-hydroxyethyl)amino-4-N-(β-hydroxyethyl)aminonitrobenzene,
2-amino-5-N-(β-aminoethyl)aminonitrobenzene,
2-N-(β-aminoethyl)amino-5-methoxynitrobenzene,
2-N-(methyl)amino-5-N-(β-amino ethyl)aminonitrobenzene,
2-N-(β-aminoethyl)amino-4-N,N-(dimethyl)aminonitrobenzene,
3-amino-4-N-(β-aminoethyl)aminonitrobenzene,
2-amino-4-methyl 5-N-(β-aminoethyl)aminonitrobenzene,
2-N-(β-aminoethyl)amino-5-N,N-bis(β-hydroxyethyl)aminonitrobenzene,
3-β-aminoethyloxy-4-aminonitrobenzene,
2-N-(methyl)amino-5-(N-δ-amino-n-butyl)aminonitrobenzene,
2-N-(γ-amino-n-propyl)amino-5-N,N-(dimethyl)aminonitrobenzene,
3-methoxy 4-N-(β-amino ethyl)aminonitrobenzene,
2-N-(β-aminoethyl)amino-5-aminonitrobenzene,
2-amino-4-chloro 5-N-(β-amino ethyl)aminonitrobenzene,
2-N-(β-aminoethyl)amino-4-methoxynitrobenzene,
2-N-(β-aminoethyl)aminonitrobenzene,
2-N-(β-aminoethyl)amino-5-N-(β-aminoethyl)aminonitrobenzene,
2-N-(β-aminoethyl)amino-4-β-hydroxyethyloxynitrobenzene,
3-β-hydroxyethyloxy-4-N-(β-aminoethyl)aminonitrobenzene,
2-amino-5-aminoethyloxynitrobenzene,
3-hydroxy 4-N-(β-aminoethyl)aminonitrobenzene,
2-N-(β-aminoethyl)amino-5-β-hydroxyethyloxynitrobenzene,
2-N-(β-aminoethyl)amino-4-hydroxynitrobenzene,
1'-[hydroxy-2 N-(β-hydroxyethyl)amino-3-nitro-6]benzyloxy]-2 ethylamine, and
1'-[hydroxy-2 N-(β-hydroxypropyl)amino-3-nitro-6]benzyloxy]-2 ethylamine.

Among the nitrobenzene dyes of formula (XXIX) above, preference is most particularly given to:

2-amino-4-methyl-5-N-(β-hydroxyethyl)aminonitrobenzene,
4-N-(β-ureidoethyl)aminonitrobenzene,
4-(N-ethyl N-β-hydroxyethyl)amino-1-N-(β-hydroxyethyl) aminonitrobenzene,
2-N-(β-hydroxyethyl)amino-5-methylnitrobenzene,
5-chloro 3-N-(ethyl)amino-4-hydroxynitrobenzene,
le 5-amino-3-chloro 4-hydroxynitrobenzene,
2-N-(γ-hydroxypropyl)amino-5-N,N-bis(β-hydroxyethyl) aminonitrobenzene,
5-hydroxy-2-N-(γ-hydroxypropyl)aminonitrobenzene,
1,3-bis-(β-hydroxyethyl)amino-4-chloro-6-nitrobenzene,
3,4-diaminonitrobenzene,
2-amino-5-hydroxynitrobenzene,
2-amino-3-hydroxynitrobenzene,
2-amino 5-N-(β-hydroxyethyl)aminonitrobenzene,
2-amino-5-N,N-bis-(β-hydroxyethyl)aminonitrobenzene,
2-N-(β-hydroxyethyl)amino-5-N,N-bis(β-hydroxyethyl) aminonitrobenzene,
2-N-(β-hydroxyethyl)amino-5-hydroxynitrobenzene,
2-N-(β-hydroxyethyl)amino-5-aminonitrobenzene,
2-N-(β-aminoethyl)amino-4-methoxynitrobenzene, and
2-N-(β-aminoethyl)amino-5-β-hydroxyethyloxynitrobenzene.

The direct dye(s) preferably represent(s) from 0.0005% to 15% by weight approximately, relative to the total weight of the composition containing it (them), and even more preferentially from 0.005% to 10% by weight approximately, relative to this weight. Preferentially, the direct dye(s) represent(s) at least 0.1% by weight, preferably at least 0.5% by weight, more preferentially from 0.5% 5% by weight, relative to the total weight of the competition containing it (them).

According to one particular embodiment of the invention, the composition (B) of the process comprises b) one or more oxidation dyes.

The oxidation dye(s) is (are) chosen from one or more oxidation bases, optionally combined with one or more couplers.

According to one preferred embodiment, the oxidation bases are chosen from para-phenylenediamines, bis(phenyl) alkylenediamines, para-aminophenols, ortho-aminophenols and heterocyclic bases, and the corresponding addition salts.

Among the para-phenylenediamines that may be mentioned are, for example, para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the corresponding addition salts with an acid.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the corresponding addition salts with an acid, are particularly preferred.

Among the bis(phenyl)alkylenediamines that may be mentioned, for example, are N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the corresponding addition salts.

Among the para-aminophenols that are mentioned are, for example, para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethyl-aminomethyl)phenol and 4-amino-2-fluorophenol, and the corresponding addition salts with an acid.

Among the ortho-aminophenols that may be mentioned, for example, are 2-aminophenol, 2-amino-5-methylphenol, 2-amino-6-methylphenol and 5-acetamido-2-aminophenol, and the corresponding addition salts.

Among the heterocyclic bases that may be mentioned, for example, are pyridine, pyrimidine and pyrazole derivatives.

Among the pyridine derivatives that may be mentioned are the compounds described, for example, in patents GB 1 026 978 and GB 1 153 196, for example 2,5-diaminopyridine, 2-(4-methoxyphenyl)amino-3-aminopyridine and 3,4-diaminopyridine, and the corresponding addition salts.

Other pyridine oxidation bases that are useful in the present invention are the 3-aminopyrazolo[1,5-a]pyridine oxidation bases or the corresponding addition salts described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol, 2-β-hydroxyethoxy-3-aminopyrazolo[1,5-a]pyridine and 2-(4-dimethylpiperazinium-1-yl)-3-aminopyrazolo[1,5-a]pyridine, and the corresponding addition salts.

More particularly, the oxidation bases that are useful in the present invention are chosen from 3-aminopyrazolo[1,5-a]pyridines and are preferably substituted on carbon atom 2 with:

a) a (di)($C_1$-$C_6$)(alkyl)amino group, said alkyl group possibly being substituted with at least one hydroxyl, amino or imidazolium group;

b) an optionally cationic 5- to 7-membered heterocycloalkyl group comprising from 1 to 3 heteroatoms, optionally substituted with one or more ($C_1$-$C_6$)alkyl groups such as a di($C_1$-$C_4$)alkylpiperazinium group; or c) a ($C_1$-$C_6$)alkoxy group optionally substituted with one or more hydroxyl groups, such as a β-hydroxyalkoxy group, and the corresponding addition salts.

Among the pyrimidine derivatives that may be mentioned are the compounds described, for example, in patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazole derivatives that may be mentioned are the compounds described in patents DE 3843892 and DE 4133957 and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the corresponding addition salts. Use may also be made of 4,5-diamino-1-(β-methoxyethyl)pyrazole.

A 4,5-diaminopyrazole will preferably be used and even more preferentially 4,5-diamino-1-(β-hydroxyethyl)pyrazole and/or a corresponding salt.

The pyrazole derivatives that may also be mentioned include diamino-N,N-dihydropyrazolopyrazolones and in particular those described in patent application FR-A-2 886 136, such as the following compounds and the corresponding addition salts: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H, 5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-bis(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H, 5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one and 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a corresponding salt.

Heterocyclic bases that will preferably be used include 4,5-diamino-1-(β-hydroxyethyl)pyrazole and/or 2,3-diamino-6,7-dihydro-1H,5H-pyrazolo[1,2-a]pyrazol-1-one and/or a corresponding salt.

The composition according to the invention may optionally comprise one or more coupling agents advantageously chosen from those conventionally used in the dyeing of keratin fibres.

Among these coupling agents, mention may be made in particular of meta-phenylenediamines, meta-aminophenols, meta-diphenols, naphthalene-based coupling agents and heterocyclic coupling agents, and also the corresponding addition salts.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, 2-methyl-5-aminophenol, 5-N-(β-hydroxyethyl)amino-2-methylphenol, 3-aminophenol and 3-amino-2-chloro-6-methylphenol, the corresponding addition salts with an acid and the corresponding mixtures.

In general, the addition salts of oxidation bases and couplers that may be used in the context of the invention are chosen in particular from the addition salts with an acid such as the hydrochlorides, hydrobromides, sulfates, citrates, succinates, tartrates, lactates, tosylates, benzenesulfonates, phosphates and acetates.

The oxidation base(s) each advantageously represent from 0.001% to 10% by weight relative to the total weight of the composition, and preferably from 0.005% to 5% by weight relative to the total weight of the composition and of the ready-to-use composition.

The coupler(s), if it (they) are present, each advantageously represents from 0.001% to 10% by weight relative to the total weight of the composition, and preferably from 0.005% to 5% by weight relative to the total weight of the composition and of the ready-to-use composition.

In particular, when the process for treating keratin fibres of the invention uses b) one or more oxidation dyes, said oxidation dye(s) is (are) used in the composition (B) in the absence of oxidizing agent, then, after steps i) and ii), an oxidizing composition comprising one or more chemical oxidizing agents is applied, optionally followed by a step of rinsing, washing and/or rinsing, and then iii) a step of heat treatment of the keratin fibres by means of a heating object.

In one preferred embodiment, the process according to the invention preferably comprises a step o) of using a composition (C) containing one or more non-thiol-comprising reducing agents after step i) and/or ii) and before the heat treatment step iii).

According to one particular embodiment of the invention, the non-thiol-comprising reducing agent(s) present in the composition (C) according to the invention is (are) chosen from ortho-diphenol derivatives having reducing properties. In a manner known per se, the term "ortho-diphenol" denotes compounds comprising at least one aromatic ring, preferably a benzene ring, comprising at least two hydroxyl (OH) groups borne by two adjacent carbon atoms of the aromatic ring which in addition do not comprise a mercapto or disulfide group.

The aromatic ring may more particularly be a fused aryl or fused heteroaromatic ring, i.e. optionally comprising one or more heteroatoms, such as benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline and isoquinoline, said aromatic ring comprising at least two hydroxyl groups borne by two adjacent carbon atoms of the aromatic ring. Preferentially, the aromatic ring of the ortho-diphenol derivatives according to the invention is a benzene ring.

The term "fused ring" is intended to mean that at least two saturated or unsaturated and heterocyclic or non-heterocyclic rings have a common bond, i.e. that at least one ring is joined side by side with another ring.

The ortho-diphenols according to the invention may or may not be salified. They can also be in the aglycone form (without bonded sugar) or in the form of glycosylated compounds.

More particularly, the ortho-diphenol derivative represents a compound of formula (XXXI), or an oligomer thereof, in salified or non-salified form:

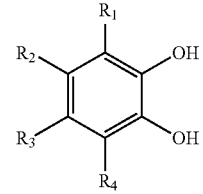

(XXXI)

in which formula (XXXI) the substituents:
$R_1$ to $R_4$, which may be identical or different, represent:
a hydrogen atom,
a halogen atom,
a hydroxyl radical,
a carboxyl radical;
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkoxy radical,
an alkoxyalkyl radical,
an alkoxyaryl radical, it being possible for the aryl group to be optionally substituted,
an aryl radical,
a substituted aryl radical, a saturated or unsaturated heterocyclic radical carrying or not carrying a cationic or anionic charge, optionally substituted and/or optionally fused with an aromatic ring, preferably a benzene ring, said aromatic ring being optionally substituted, in particular with one or more hydroxyl or glycosyloxy groups, a radical containing one or more silicon atoms, or two of the substituents carried by two adjacent carbon atoms $R_1$-$R_2$, $R_2$-$R_3$ or $R_3$-$R_4$ form, together with the carbon atoms carrying them, a saturated or unsaturated and aromatic or non-aromatic ring, optionally comprising one or more heteroatoms and optionally fused with one or more saturated or unsaturated rings optionally comprising one or more heteroatoms. Particularly, $R_1$ to $R_4$ together form from one to four rings.

A specific embodiment of the invention relates to ortho-diphenol derivatives of formula (XXXI), two adjacent substituents $R_1$-$R_2$, $R_2$-$R_3$ or $R_3$-$R_4$ of which cannot form, with the carbon atoms which carry them, a pyrrolyl radical. More particularly, $R_2$ and $R_3$ cannot form a pyrrolyl radical fused to the benzene ring bearing the two hydroxyls.

The ortho-diphenols of use in the process of the invention can be natural or synthetic. The natural ortho-diphenols include the compounds which may be present in nature and which are reproduced by chemical (semi)synthesis.

The salts of the ortho-diphenols of the invention can be salts of acids or of bases. The acids can be mineral or organic. Preferably, the acid is hydrochloric acid, which results in chlorides.

The bases can be mineral or organic. In particular, the bases are alkali metal hydroxides, such as sodium hydroxide, which results in sodium salts.

According to one particular embodiment of the invention, the composition(s) comprise(s) as ingredient one or more synthetic ortho-diphenol derivative(s) that do (does) not exist in nature.

According to another preferred embodiment of the invention, the process for relaxing curls of keratin fibres uses, as non-thiol-comprising agent, one or more natural ortho-diphenol derivative(s).

More particularly, the ortho-diphenols that may be used in the process of the invention are in particular:

flavanols, such as catechin and epicatechin gallate,
flavonols, such as quercetin,
anthocyanidins, such as cyanidin, delphinidin or petunidin,
anthocyanins or anthocyans, for instance myrtillin,
ortho-hydroxybenzoates, for example gallic acid salts,
flavones, such as luteolin,
hydroxystilbenes, for example 3,3',4,5'-tetrahydroxystilbene, optionally oxylated (for example glucosylated),
3,4-dihydroxyphenylalanine and the derivatives thereof,
2,3-dihydroxyphenylalanine and the derivatives thereof,
4,5-dihydroxyphenylalanine and the derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and the derivatives thereof,
1,2,4-trihydroxybenzene and the derivatives thereof,
1,2,3-trihydroxybenzene and the derivatives thereof,
2,4,5-trihydroxytoluene and the derivatives thereof,
proanthocyanidins and especially the proanthocyanidins A1, A2, B1, B2, B3 and C1,
proanthocyanins,
tannic acid,
ellagic acid,
and the mixtures of the preceding compounds.

When the dyeing precursors exhibit D and L forms, both forms can be used in the compositions according to the invention, as can the racemates.

According to one embodiment, the natural ortho-diphenols result from extracts of animals, bacteria, fungi, algae or plants, used in their entirety or partially. In particular as regards plants, the extracts are derived from plants or plant parts, such as fruit, including citrus fruit, vegetables, trees or shrubs. Use may also be made of mixtures of these extracts rich in ortho-diphenols as defined above.

Preferably, the natural ortho-diphenol(s) of the invention is (are) derived from plants or plant parts.

The extracts are obtained by extraction from various plant parts, such as, for example, the root, the wood, the bark, the leaf, the flower, the fruit, the seed, the pod or the peel.

Use may also be made of mixtures of plant extracts.

According to a specific embodiment of the invention, the ortho-diphenol derivative(s) are natural extracts rich in ortho-diphenols. According to a preferred form, the ortho-diphenol derivative(s) are solely natural extracts.

The natural extracts according to the invention may be in the form of powders or liquids. Preferably, the extracts of the invention are provided in the form of powders.

According to one particular embodiment of the invention, the non-thiol-comprising reducing agent(s) present in the composition (C) according to the invention is (are) chosen from meta-hydroxyphenol derivatives, also called resorcinols, having reducing properties. In a manner known per se, the term "resorcinols" denotes compounds which comprise at least one aromatic ring, preferably a benzene ring, comprising at least two hydroxyl (OH) groups borne by two carbon atoms which are in the meta-position with respect to one another, and which also do not comprise a mercapto or disulfide group.

The aromatic ring may more particularly be a fused aryl or fused heteroaromatic ring, i.e. optionally comprising one or more heteroatoms, such as benzene, naphthalene, tetrahydronaphthalene, indane, indene, anthracene, phenanthrene, isoindole, indoline, isoindoline, benzofuran, dihydrobenzofuran, chroman, isochroman, chromene, isochromene, quinoline, tetrahydroquinoline and isoquinoline, said aromatic ring comprising at least two hydroxyl groups borne by two carbon atoms which are in the meta-position with respect to one another. Preferentially, the aromatic ring of the resorcinol derivatives according to the invention is a benzene ring.

According to one more particular embodiment of the invention, the non-thiol-comprising reducing agent(s) present in the composition(s) used according to the invention is (are) chosen from meta-hydroxyphenol derivatives of formula (XXXII), and also the organic or mineral acid or base salts thereof, and the solvates thereof such as hydrates:

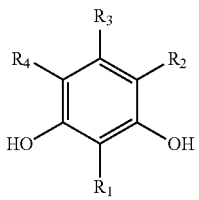

(XXXII)

in which formula (XXXII) the substituents:
$R_1$, $R_2$ and $R_4$, which may be identical or different, represent:
a hydrogen atom,
a halogen atom,
a carboxyl radical,
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkylcarbonyl radical,
a carboxaldehyde radical,
an alkoxy radical,
an alkoxyalkyl radical,
an alkoxyaryl radical, it being possible for the aryl group to be optionally substituted,
an arylalkylcarbonyl radical of which the aryl group, particularly phenyl group, is optionally substituted, preferably with one or more hydroxyl groups,
an aryl radical,
a substituted aryl radical,
a saturated or unsaturated heterocyclic radical carrying or not carrying a cationic or anionic charge, optionally substituted and/or optionally fused with an aromatic ring, preferably a benzene ring, said aromatic ring being optionally substituted, in particular with one or more hydroxyl or glycosyloxy groups,
a radical containing one or more silicon atoms,
$R_3$ represents:
a hydrogen atom,
a halogen atom,
a hydroxyl radical,
a carboxyl radical,
an alkyl carboxylate or alkoxycarbonyl radical,
an optionally substituted amino radical,
an optionally substituted and linear or branched alkyl radical,
a linear or branched alkenyl radical which is optionally substituted, in particular with a phenyl group which is preferably optionally substituted with one or more (di)($C_1$-$C_4$)(alkyl)amino, or hydroxyl groups,
an optionally substituted cycloalkyl radical,
an alkylcarbonyl radical,
a carboxaldehyde radical,
an alkoxy radical,
an alkoxyalkyl radical,
an alkoxyaryl radical, it being possible for the aryl group to be optionally substituted,
an aryl radical,
a substituted aryl radical,
a saturated or unsaturated heterocyclic radical carrying or not carrying a cationic or anionic charge, optionally substituted and/or optionally fused with an aromatic ring, preferably a benzene ring, said aromatic ring being optionally substituted, in particular with one or more hydroxyl or glycosyloxy groups,
a radical containing one or more silicon atoms,
or two of the substituents borne by two adjacent carbon atoms $R_2$-$R_3$ or $R_3$-$R_4$ form, together with the carbon atoms carrying them, a saturated or unsaturated and non-aromatic ring, optionally comprising one or more heteroatoms and optionally fused with one or more saturated or unsaturated rings optionally comprising one or more heteroatoms. Particularly, $R_2$ to $R_4$ together form from two to four rings.

More particularly, the non-thiol-comprising reducing agent(s) present in the composition (C) according to the invention is (are) chosen from meta-hydroxyphenols of formula (XXXII) in which the substituents:
$R_1$, $R_3$ and $R_4$, which may be identical or different, represent:
a hydrogen atom,
a halogen atom,
a carboxyl radical,
an alkyl carboxylate or alkoxycarbonyl radical,
an optionally substituted amino radical,
an optionally substituted and linear or branched alkyl radical,
a linear or branched alkenyl radical which is optionally substituted, in particular with a phenyl group which is preferably optionally substituted with one or more (di)($C_1$-$C_4$)(alkyl)amino, or hydroxyl groups,
an alkylcarbonyl radical,
a carboxaldehyde radical,
an alkoxy radical, and/or
$R_2$ represents:
a hydrogen atom,
a halogen atom,
a hydroxyl radical,
a carboxyl radical,
an alkyl carboxylate or alkoxycarbonyl radical,
an optionally substituted amino radical,
a phenylalkylcarbonyl radical of which the phenyl group is optionally substituted, preferably with one or more hydroxyl groups,
an optionally substituted and linear or branched alkyl radical,
an optionally substituted and linear or branched alkenyl radical,
an alkylcarbonyl radical,
a carboxaldehyde radical,
an alkoxy radical.

More particularly, the substituent $R_2$ in formula (XXXII) represents a hydrogen atom or a ($C_1$-$C_6$)alkyl group, preferably a hydrogen atom.

According to one particular embodiment of the invention, the non-thiol-comprising reducing agent(s) present in the composition (C) according to the invention is (are) chosen from resorcinol derivatives of formula (XXXII), and also the organic or mineral acid or base salts thereof, and the solvates thereof such as hydrates: in which $R^1$ to $R^4$, which may be identical or different, represent a hydrogen or halogen atom, or a group chosen from:
optionally substituted ($C_1$-$C_{10}$)alkyl, in particular optionally substituted with at least one hydroxyl radical;
optionally substituted ($C_2$-$C_{10}$)alkenyl, in particular optionally substituted with at least one aryl group, such as a phenyl group, which is optionally substituted with one or more (di)($C_1$-$C_4$)(alkyl)amino, or hydroxyl groups;

($C_1$-$C_{10}$)alkoxy;

carboxy —C(O)—OH or carboxylate —C(O)—O—, M⁺; with M⁺ representing a cationic counterion such as an alkali metal or alkaline-earth metal, or an ammonium;

ester —C(O)—O—$R^5$ or —O—C(O)—$R^5$, with $R^5$ representing a ($C_1$-$C_{10}$)alkyl group, particularly —C(O)—O—$R^5$;

amido —C(O)—$NR^6R^7$ or —$NR^6$—C(O)—$R^7$ with $R^6$ and $R^7$, which may be identical or different, representing a hydrogen atom or a ($C_1$-$C_{10}$)alkyl group, particularly —C(O)—$NH_2$;

($C_1$-$C_{10}$)alkylcarbonyl;

hydroxyl; and amino —$NR^8R^9$, with $R^8$ and $R^9$, which may be identical or different, representing a hydrogen atom or a group ($C_1$-$C_{10}$)alkyl, particularly —$NH_2$;

In particular, in formula (XXXII), $R_1$, $R_2$ and $R_4$ represent a hydrogen atom or an optionally substituted ($C_1$-$C_6$)alkyl group, preferably hydrogen, and/or $R_3$ represents a hydrogen atom or a linear or branched ($C_1$-$C_6$)alkyl or ($C_2$-$C_6$)alkenyl group, such as ethanyl, optionally substituted with an aryl group, such as a phenyl group, which is optionally substituted, preferably with one or more (di)($C_1$-$C_4$)(alkyl)amino, or hydroxyl groups.

More preferentially, the non-thiol-comprising reducing agent(s) present in the composition(s) used according to the invention is (are) chosen from the resorcinol derivative of formula (XXXII), in which $R_1$, $R_2$ and $R_4$ represent a hydrogen atom or a ($C_1$-$C_4$)alkyl group, preferably hydrogen, and $R_3$ represents a hydrogen atom or an Ar—CH=CH— group with Ar representing an aryl group, in particular a phenyl group, said aryl group being optionally substituted, preferably with one or more hydroxyl groups; in particular said hydroxyl group(s) is (are) substituted in the ortho or para position with respect to the phenyl group.

Preferably, the meta-hydroxyphenols according to the invention do not comprise two hydroxyl groups borne by two adjacent carbons.

The meta-hydroxyphenols of the invention may be natural or synthetic. Among the natural meta-hydroxyphenols are compounds that may be present in nature and that are reproduced by chemical (semi)synthesis. The salts of the meta-hydroxyphenols of the invention can be salts of acids or of bases. The acids can be mineral or organic. Preferably, the acid is hydrochloric acid, which results in chlorides. The bases can be mineral or organic. In particular, the bases are alkali metal hydroxides, such as sodium hydroxide, which results in sodium salts.

According to a particular embodiment of the invention, the composition comprises, as ingredient a), one or more synthetic meta-hydroxyphenol(s) derivative(s) that do not exist in nature.

According to one embodiment, the natural meta-hydroxyphenols are derived from extracts of animals, bacteria, fungi, algae, plants and fruits, used in their entirety or partially. In particular regarding plants, the extracts are derived from fruits, including citrus fruits, from vegetables, from trees and from shrubs. Use may also be made of mixtures of these extracts, which are rich in meta-hydroxyphenols as defined above.

According to one particular embodiment of the invention, the non-thiol-comprising reducing agent(s) present in the composition (C) according to the invention is (are) chosen from para-hydroxyphenol derivatives having reducing properties. In a manner known per se, the term "para-hydroxyphenol" denotes compounds which comprise at least one aromatic ring, preferably a benzene ring, comprising at least two hydroxyl (OH) groups borne by two carbon atoms which are in the para-position with respect to one another, and which also do not comprise a mercapto or disulfide group.

According to one more particular embodiment of the invention, the non-thiol-comprising reducing agent(s) present in the composition (C) is (are) chosen from para-hydroxyphenol derivatives of formula (XXXIII), and also the organic or mineral acid or base salts thereof, and the solvates thereof such as hydrates:

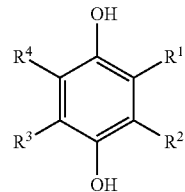

(XXXIII)

in which formula (XXXIII) $R^1$ to $R^4$, which may be identical or different, are as defined previously for formulae (XXXI) or (XXXII), preferably represent a hydrogen atom or an optionally substituted ($C_1$-$C_4$)alkyl group, preferably hydrogen.

Preferentially, the non-thiol-comprising agent(s) is (are) chosen from catechol, gallic acid, para-hydroxyphenol or resveratrol, it being understood that, when the aromatic ring of the ortho diphenols, meta hydroxyphenols or para-hydroxyphenols bear more than 2 hydroxyl groups (for example 3, 4, etc.), the compounds should be understood according to the following rule:

If 3 hydroxyl groups are adjacent on the aromatic ring: (position 1, 2, 3 for example), then said non-thiol-comprising reducing agent will be considered to be an ortho-diphenol.

If there are 3 hydroxyl groups of which two are adjacent on the aromatic ring and one is opposite (positions 1, 2, 4 or 1, 2, 5), then said non-thiol-comprising reducing agent will be considered to be a para-hydroxyphenol.

If there are 3 hydroxyl groups of which none is adjacent (position 1, 3, 5), then said non-thiol-comprising reducing agent will be considered to be a meta-hydroxyphenol.

Preferentially, the non-thiol-comprising reducing agent(s) represent(s) from 1% to 10% by weight and preferably from 2% to 8% by weight relative to the total weight of the composition (C) containing it (them).

When the process of the invention comprises step o) of applying the composition (C), the weight ratio between the amount of thiol-comprising reducing agent(s) and the amount of non-thiol-comprising reducing agent(s) is between 0.01 and 10, particularly between inclusively 0.1 and 5, and more preferentially between inclusively 0.2 and 1.

In one embodiment, the pH of the composition (C) is between inclusively 1 and 5, preferably between 2.5 and 4.

In one embodiment, the pH of the composition (A) is between inclusively 1 and 5, preferably between 2.5 and 4.

In one particular embodiment of the invention, the composition (C) comprising the non-thiol-comprising agent(s) is generally applied before and/or after the composition (A) comprising the thiol-comprising agent(s), and preferably after the composition (A). In other words, in this variant, the process according to the invention comprises step i) of applying the composition (A), step o) of applying the composition (C), step ii) of applying the composition (B), then iii) the heating step. This alternative is preferred.

In this preferred embodiment, the process of the invention preferably does not comprise a step of rinsing the keratin fibres between step i) and step o) before step ii) of applying the composition (B).

Most particularly preferably in this embodiment, the process comprises:
the application to the fibres of a composition (A) comprising said thiol-comprising agent(s) at a pH of between 1 and 5, then
an optional step of rinsing the fibres, then
the application to the fibres of a composition (C) comprising said non-thiol-comprising agent(s),
the application to the fibres of a composition (B) comprising said direct dye(s), then
a step of heat treatment of the fibres by means of a heating tool.

According to one particular embodiment of the invention, the composition(s) used in the process according to the invention can also comprise one or more non-ionic, anionic, cationic, or amphoteric or zwitterionic surfactants.

Surfactants

The composition according to the present invention may optionally also comprise one or more surfactants.

The surfactant(s) that may be used in the composition according to the invention may be chosen from non-ionic surfactants, cationic surfactants, anionic surfactants and amphoteric or zwitterionic surfactants, and mixtures thereof.

The composition according to the present invention may thus comprise one or more non-ionic surfactants.

The non-ionic surfactants that may be used are described, for example, in the *Handbook of Surfactants* by M. R. Porter, published by Blackie & Son (Glasgow and London), 1991, pp. 116-178.

Examples of non-ionic surfactants that may be mentioned include the following non-ionic surfactants:
oxyalkylenated ($C_8$-$C_{24}$)alkylphenols;
saturated or unsaturated, linear or branched, oxyalkylenated or glycerolated $C_8$-$C_{40}$ alcohols, comprising one or two fatty chains;
saturated or unsaturated, linear or branched, oxyalkylenated $C_8$-$C_{30}$ fatty acid amides;
esters of saturated or unsaturated, linear or branched, $C_8$-$C_{30}$ acids and of polyethylene glycols;
preferably oxyethylenated esters of saturated or unsaturated, linear or branched, $C_8$-$C_{30}$ acids and of sorbitol;
esters of fatty acids and of sucrose;
($C_5$-$C_{30}$)alkyl(poly)glucosides, ($C_5$-$C_{30}$)alkenyl(poly)glucosides, which are optionally oxyalkylenated (0 to 10 oxyalkylene units) and comprising from 1 to 15 glucose units, ($C_8$-$C_{30}$)alkyl(poly)glucoside esters;
saturated or unsaturated oxyethylenated plant oils;
condensates of ethylene oxide and/or of propylene oxide;
N—($C_8$-$C_{30}$)alkylglucamine and N—($C_8$-$C_{30}$)acylmethylglucamine derivatives;
aldobionamides;
amine oxides;
oxyethylenated and/or oxypropylenated silicones;
and mixtures thereof.

The oxyalkylene units are more particularly oxyethylene or oxypropylene units, or their combination, preferably oxyethylene units.

The number of moles of ethylene oxide and/or of propylene oxide preferably ranges from 1 to 250, more particularly from 2 to 100 and better still from 2 to 50; the number of moles of glycerol ranges in particular from 1 to 50 and better still from 1 to 10.

Advantageously, the non-ionic surfactants according to the invention do not comprise any oxypropylene units.

As examples of glycerolated non-ionic surfactants, use is preferably made of monoglycerolated or polyglycerolated $C_8$-$C_{40}$ alcohols, comprising from 1 to 50 mol of glycerol and preferably from 1 to 10 mol of glycerol.

Preference is more particularly given, among the glycerolated alcohols, to the use of the $C_8$/$C_{10}$ alcohol comprising 1 mol of glycerol, the $C_{10}$/$C_{12}$ alcohol comprising 1 mol of glycerol and the $C_{12}$ alcohol comprising 1.5 mol of glycerol.

The non-ionic surfactant(s) that may be used in the dye composition according to the invention are preferentially chosen from:
oxyethylenated $C_8$ to $C_{40}$ alcohols comprising from 1 to 100 mol of ethylene oxide, preferably from 2 to 50 and more particularly from 2 to 40 mol of ethylene oxide and comprising one or two fatty chains;
saturated or unsaturated oxyethylenated vegetable oils comprising from 1 to 100 and preferably from 2 to 50 mol of ethylene oxide;
($C_5$-$C_{30}$)alkyl(poly)glucosides, which are optionally oxyalkylenated (0 to 10 OE) and comprising 1 to 15 glucose units;
monoglycerolated or polyglycerolated $C_8$ to $C_{40}$ alcohols, comprising from 1 to 50 mol of glycerol and preferably from 1 to 10 mol of glycerol;
saturated or unsaturated, linear or branched, oxyalkylenated $C_8$-$C_{30}$ fatty acid amides;
esters of saturated or unsaturated, linear or branched, $C_8$-$C_{30}$ acids and of polyethylene glycols;
and mixtures thereof.

The composition according to the present invention can comprise one or more cationic surfactants.

"Cationic surfactant" is understood to mean a surfactant which is positively charged when it is present in the compositions according to the invention. This surfactant can carry one or more permanent positive charges or can contain one or more cationizable functional groups within the compositions according to the invention.

The cationic surfactant or surfactants are preferably chosen from primary, secondary or tertiary fatty amines which are optionally polyoxyalkylenated, or their salts, quaternary ammonium salts, and mixtures thereof.

The fatty amines generally comprise at least one $C_8$ to $C_{30}$ hydrocarbon-based chain.

As quaternary ammonium salts, mention may in particular be made of those corresponding to the general formula below:

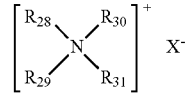

in which the groups $R_{28}$ to $R_{31}$, which may be identical or different, represent a linear or branched aliphatic group containing from 1 to 30 carbon atoms, or an aromatic group such as aryl or alkylaryl, at least one of the groups $R_{28}$ to $R_{31}$ denoting a group containing from 8 to 30 carbon atoms, preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate, and $C_1$-$C_{30}$ hydroxyalkyl groups, $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

The anion $X^-$ is preferably a halide (chloride, bromide or iodide) or an alkyl sulfate, more particularly methyl sulfate. However, use may be made of methanesulfonate, phosphate, nitrate, tosylate, an anion derived from an organic acid, such as acetate or lactate, or any other anion that is compatible with the ammonium bearing an ester function.

The composition according to the present invention may comprise one or more anionic surfactants.

The term "anionic surfactant" is intended to mean a surfactant comprising, as ionic or ionizable groups, only anionic groups. These anionic groups are preferably chosen from the groups —COOH, —COO—, —$SO_3H$, —$SO_3^-$, —$OSO_3H$, —$OSO_3^-$, —$PO_2H_2$, —$PO_2H^-$, —$PO_2^{2-}$, —$P(OH)_2$, $=P(O)OH$, —$P(OH)O$—, $=P(O)O$—, $=POH$ and $=PO$—, the anionic parts comprising a cationic counterion such as an alkali metal, an alkaline-earth metal or an ammonium.

The composition according to the present invention can comprise one or more amphoteric or zwitterionic surfactants.

In particular, the amphoteric or zwitterionic surfactant(s), which are preferably non-silicone, which may be used in the composition according to the present invention may in particular be derivatives of secondary, tertiary or optionally quaternized aliphatic amines, in which derivatives the aliphatic group is a linear or branched chain comprising from 8 to 22 carbon atoms, said amine derivatives containing at least one anionic group, for instance a carboxylate, sulfonate, sulfate, phosphate or phosphonate group.

The surfactants that can be used in the process according to the invention are preferably non-ionic or cationic.

When they are present, the surfactant(s) preferably represent from 0.1% to 20% by weight and better still from 1% to 10% by weight relative to the total weight of each composition containing it (them).

The composition(s) that can be used in the process according to the invention generally comprise(s) water, which typically represents from 10% to 90% by weight, preferably from 10% to 80% by weight, preferably from 10% to 70% by weight, relative to the total weight of each composition.

The compositions that can be used in the process according to the invention may also contain cosmetically acceptable organic solvents other than those contained in the composition (B), more particularly including alcohols such as ethyl alcohol, isopropyl alcohol, benzyl alcohol and phenylethyl alcohol, or polyols or polyol ethers, for instance ethylene glycol monomethyl, monoethyl or monobutyl ethers, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

The solvents may then represent from 0.5% to 20% by weight and preferably from 2% to 10% by weight relative to the total weight of each composition containing them.

The compositions used according to the invention may also comprise one or more cosmetic adjuvants other than the compounds described previously.

For example, they may comprise one or more standard additive(s) that are well known in the art, such as linear or cyclic, volatile or non-volatile silicones, cationic, non-ionic, anionic or amphoteric polymers, peptides and derivatives thereof, protein hydrolysates, waxes, agents for preventing hair loss, vitamins and provitamins including panthenol, sunscreens, mineral or organic pigments, sequestrants, plasticizers, solubilizers, mineral or organic thickeners, antioxidants, nacreous agents, fragrances and preservatives.

Needless to say, those skilled in the art will take care to select this or these optional additional compound(s) such that the advantageous properties intrinsically associated with the compositions used according to the invention are not, or are not substantially, adversely affected by the envisaged addition(s).

The above additives may generally be present in an amount, for each of them, of between 0 and 20% by weight relative to the total weight of the composition containing them.

Those skilled in the art can choose the appropriate formulation form for the compositions according to the invention, and also their methods of preparation, on the basis of their general knowledge, taking into account first the nature of the constituents used, in particular their solubility in the support, and secondly the application envisaged for the composition. Thus, the composition(s) according to the invention may be in the form of a suspension or a dispersion, in particular of oil-in-water by means of vesicles; an optionally thickened or even gelled oily solution; an oil-in-water, water-in-oil or multiple emulsion; a gel or a mousse; an oily or emulsified gel; a dispersion of vesicles, in particular lipid vesicles; a two-phase or multiphase lotion; a spray. These compositions can have the appearance of a lotion, a cream, a salve, a soft paste, an ointment, a solid that has been cast or moulded in particular as a stick or in a dish, or a compacted solid.

The compositions used in the process according to the invention can thus be in any form compatible with an application to keratin fibres, for example in the form of a wax, a paste, a more or less fluid or thick cream, gel, foam, a spray or a lotion.

The compositions described previously are applied to dry or wet keratin fibres, sequentially or simultaneously.

The compositions are usually left in place on the fibres for a time generally ranging from 1 minute to 1 hour and preferably from 5 minutes to 30 minutes for each composition.

As described previously, the process according to the invention comprises a step of heat treatment of the fibres by means of a heating tool.

This heat treatment step is generally carried out following the application of the composition(s) described above, optionally after elimination thereof by rinsing.

Preferably, the heating tool is chosen from a hairstyling hood, a straightening iron (flat iron), a hairdryer and an infrared-ray dispenser, and more preferentially the heating tool is a straightening iron. The iron is applied by successive separate strokes lasting a few seconds or by gradual movement or sliding along the locks.

The hair treatment step is generally carried out at a temperature ranging from 30 to 250° C., preferably from 60 to 230° C. and more preferentially from 100 to 150° C.

According to one particular embodiment of the invention, the process for treating keratin fibres comprises, as heat treatment, a step of smoothing/uncurling the keratin fibres by means of a heating tool chosen from irons and a steam iron, i.e. "irons" which comprise a device that emits steam and that applies this steam before, during or after the straightening/uncurling.

The term "iron" is intended to mean, within the meaning of the present invention, a device for heating keratin fibres, said fibres and the heating device being brought into contact. The end of the iron which comes into contact with the keratin fibres generally exhibits two flat surfaces. These two surfaces can be made of metal or of ceramic. In particular, these two surfaces can be smooth or crimped or curved.

According to a particular embodiment, the iron or the steam iron is at a temperature of between 65° C. and 250° C., particularly between 80° C. and 230° C., more particularly greater than or equal to 100° C. and preferentially between 100° C. and 190° C. Preferably, the heat treatment step of the process for treating keratin fibres is carried out at a temperature ranging from 150° C. to 230° C., preferably ranging from 160° C. to 230° C., preferentially ranging from 160° C. to 210° C., especially ranging from 180° C. to 200° C.

As examples of irons that may be used in the straightening/uncurling process according to the invention, mention may be made of any type of steam flat iron, and in particular, nonlimitingly, those described in patents U.S. Pat. Nos. 5,957,140 and 5,046,516.

The steam iron may be applied by successive separate strokes lasting a few seconds or by gradual movement or sliding along the tresses of keratin fibres, especially of hair.

Preferably, the steam iron is applied in the process according to the invention with a continuous movement from the root to the tip of the hair, in one or more passes, in particular in two to twenty passes. The duration of each pass of the steam iron may range from 2 seconds to 1 minute.

Advantageously, steam is applied to keratin fibres, especially the hair, according to a flow rate of less than 5 g/min, especially of between 1 and 4 g/min.

The application of steam may be performed using any machine known per se for generating the amount of steam of use in the process of the invention. According to a particular embodiment, this machine is portable, i.e. the tank for generating steam is in contact with the part of the device comprising the steam-dispensing orifices.

The steam application step may be performed before, during or after the heating step, and preferably before.

Preferably, the step of straightening/relaxing the keratin fibres is carried out for a time that may range from 2 seconds to 30 minutes, and preferentially from 2 seconds to 20 minutes, better still from 2 seconds to 10 minutes, better still from 2 seconds to 5 minutes and even better still from 2 seconds to 2 minutes.

Preferably, step ii) is carried out with a steampod steam straightener device.

The process according to the invention may also comprise an additional step of drying the keratin fibres, after the application steps i), optionally o) and ii), and before the heat treatment step iii). The drying step can be carried out using a hand-held hairdryer or a hood dryer or by drying in the open air. The drying step is advantageously performed at a temperature ranging from 20 to 70° C.

After the step of straightening/relaxing using the steam iron, the keratin fibres may be optionally rinsed with water or washed with a shampoo. The keratin fibres are subsequently optionally dried using a hand-held hairdryer or a hood dryer or by drying in the open air.

According to one embodiment, the process according to the invention is carried out on natural keratin fibres, in particular natural hair, possibly grey hair.

The process of the invention is particularly performed on human keratin fibres, especially dyed hair.

The process according to the invention may be carried out on keratin fibres, in particular hair, which is dry or wet. Preferentially, the process is carried out on natural keratin fibres.

After the application steps of i) and ii) of the process of the invention, and before the heat treatment step iii) is carried out, the composition(s) A and/or B applied can be left for a period ranging from 1 to 60 minutes, preferably ranging from 2 to 50 minutes, preferentially ranging from 5 to 45 minutes. The leave-on time may take place at a temperature ranging from 15° C. to 45° C., preferably at ambient temperature (25° C.).

The cosmetic composition which contains the thiol-comprising reducing agents, as described previously, is advantageously applied to the keratin fibres in an amount ranging from 0.1 to 10 grams and preferably from 0.2 to 5 grams of composition per gram of keratin fibres.

The cosmetic composition which contains the non-thiol-comprising reducing agents, as described previously, is advantageously applied to the keratin fibres in an amount ranging from 0.1 to 10 grams and preferably from 0.2 to 5 grams of composition per gram of keratin fibres.

After application of the cosmetic composition(s) A and/or B to the keratin fibres, the latter may be wrung out to remove the excess composition or washed with water or with a shampoo.

The treatment process according to the invention may be carried out before, during and/or after an additional process of cosmetic treatment of the keratin fibres, such as a process for temporary relaxing of curls (relaxing of curls with curlers, a crimping iron or a straightening iron) or a process for long-lasting relaxing of curls (permanent-waving or uncurling) of the keratin fibres.

The process according to the invention may also comprise an additional step of partially pre-drying the hair fibres before the step of increasing the temperature, so as to prevent significant amounts of steam being given off, which might burn the stylist's hands and the subject's scalp. This pre-drying step can be carried out for example by means of a dryer or of a hood or else by drying in the open air.

Before and/or at the end of the process according to the invention, the keratin fibres may optionally be washed with a shampoo, followed by rinsing with water, before being dried or left to dry.

This constitutes an advantage of the present invention; from the very first implementation of the process according to the invention, including an implementation without placing the hair under tension, a substantial reduction in the volume of the head of hair is observed, while at the same time having a substantial and uniform colouration, in particular if a head of hair comprising many grey hairs is dyed. When the hair is curly, relaxation of the curls and/or better curl definition are also observed.

It is also found that the unpleasant odours that are given off during the straightening/uncurling process, or that remain on the straightened hair, are reduced by means of performing the process according to the invention.

A subject of the present invention is also an acidic composition having a pH of inclusively between 1 and 5 and containing one or more thiol-comprising reducing agents as defined previously, and one or more dyes chosen from a) direct dyes and b) oxidation dyes as defined previously, preferably in the absence of chemical oxidizing agent, and one or more non-thiol-comprising reducing agents as defined previously.

A subject of the present invention is also a kit suitable for implementing the process of the invention. This kit comprises at least two compartments:
- a first compartment comprising a composition (A) which comprises one or more thiol-comprising reducing agents, as defined above, at a pH of inclusively between 1 and 5, preferentially between 2.5 and 4,
- a second compartment comprising a composition (B) which comprises one or more direct dyes, as defined above, and
- optionally, a third compartment comprising a composition (C) which comprises one or more non-thiol-comprising reducing agents, as defined above.

The compositions of this kit are packaged in separate compartments, which may be optionally accompanied by suitable identical or different application means, such as fine brushes, coarse brushes or sponges.

The abovementioned kit may also be equipped with means for dispensing the desired mixture on the hair, such as, for instance the device described in patent FR2 586 913.

The examples that follow illustrate the present invention, and should not in any way be considered as limiting the invention.

EXAMPLES

Example 1 a) Protocol for Preparing the Compositions Used in the Process of the Invention:

Thiolactic acid is tested comparatively in solution at 1% and 8% by weight in water at pH 3.5.

Para-hydroxyphenol is tested in solution at 5% by weight in water at pH 3.5.

The following dyes 1 to 3 were tested in solution at 0.5% by weight in water: Cationic dye 1: 4-[(2-{4-[bis(2-hydroxy-ethyl)amino]phenyl}ethenyl]-1-hexylpyridinium bromide

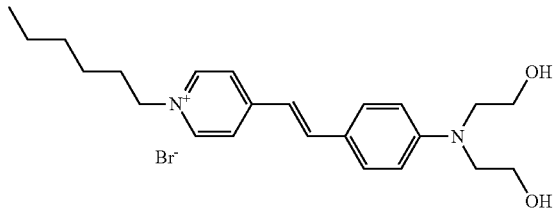 [SMILES: CCCCCC[n+]1ccc(/C=C/c2ccc(N(CCO)CCO)cc2)cc1 ; [Br-]]

Cationic Dichromophore Dye 2:

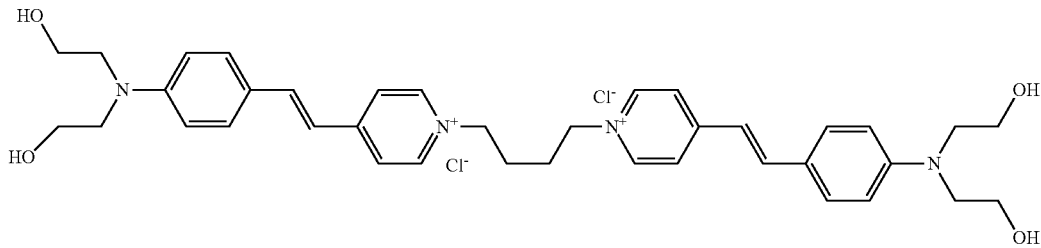 [SMILES: OCCN(CCO)c1ccc(/C=C/c2cc[n+](CCCC[n+]3ccc(/C=C/c4ccc(N(CCO)CCO)cc4)cc3)cc2)cc1 ; [Cl-] ; [Cl-]]

Neutral Direct Dye 3: 4-Amino-3-Nitrophenol b) Protocol for Evaluating the Technical Effect (Colour, Stability, Performance During/after Application)

b1) Each composition prepared in the previous preparation protocol a) was tested on natural locks containing 90% grey hairs according to dyeing/curl relaxing/straightening treatment protocols.

b2) Protocol for Brazilian straightening with conventional iron:

The locks of keratin fibres were combed, then were subjected to 10 successive blow drying passes, at position 2 (80° C.) of the hairdryer, with a round brush of medium diameter. Each of the locks was then separated into 2. Each part was subjected to 10 passes with the straightening iron using a comb on each half, then ⅔ passes over all of it at 230° C.

The locks were then washed with a mild shampoo, and dried.

c) Sensory Results of the Evaluation In Vitro

The dyed locks are subjected to 1, 10 and 20 shampooing operations according to a cycle that includes wetting the locks with water, washing with shampoos, rinsing with water followed by a drying operation.

The colour of the locks before and after washing is evaluated in the L*a*b* system, using a Minolta® CM 2002 spectrophotometer (Illuminant D65).

In the L*a*b* system, the three parameters denote respectively the intensity (L*), the shade (a*) and the saturation (b*). According to this system, the higher the value of L, the lighter or less intense is the colour. Conversely, the lower the value of L, the darker or very intense is the colour. a* and b* indicate two colour axes, a* indicates the green/red colour axis and b* indicates the blue/yellow colour axis.

The chromaticity is calculated from the measurements of a* and of b* according to the following formula:

$$C^* = \sqrt{a^{*2} + b^{*2}}$$

The higher the value of C*, the more chromatic is the colour.

The locks of hair were treated in the following way:

Lock 1 was treated with a solution containing thiolactic acid at 8% and a dye for 30 min, then rinsed, followed by a step of blow-drying and passing the iron over at 230° C.

Lock 2 was treated with a solution of thiolactic acid at 1% for 30 min, then a dyeing solution is applied for 20 min, then a solution of para-hydroxyphenol at 5% is applied for 20 min, followed by a step of blow-drying and passing the iron over at 230° C.

Lock 3 was treated with a solution of thiolactic acid at 1% for 30 min, then a solution of para-hydroxyphenol at 5% is applied for 20 min, then a dyeing solution is applied for 20 min, followed by a step of blow-drying and passing the iron over at 230° C.

Lock 4 was treated with a solution containing thiolactic acid at 1% and a dyeing solution for 30 min, then a solution of para-hydroxyphenol at 5%, followed by a step of blow-drying and passing the iron over at 230° C.

The chromaticity results are grouped together in the table below at 1 and 20 successive shampooing operations:

| | | C*1 shamp | C*20 shamp |
|---|---|---|---|
| | Lock before treatment C* 13.81 | | |
| Dye 1 | Lock 1 | 55.22 | 59.34 |
| | Lock 3 | 47.84 | 46.85 |
| Dye 2 | Lock 2 | 37.13 | 33.54 |
| | Lock 4 | 36.65 | 31.09 |
| Dye 3 | Lock 1 | 49.58 | 48.87 |
| | Lock 3 | 49.84 | 51.37 |

It appears that the colour obtained with the dyeing process is very chromatic compared with the result for chromaticity of the fibre before treatment. In addition, it appears that the chromaticity remains very intense even after 20 shampooing operations for the various dyes of the invention.

e) Composition Examples

| Active agent | Composition Formula Thiol-comprising reducing agent 8% at pH 3.5 | Composition Formula Thiol-comprising reducing agent 1% at pH 3.5 | Composition Formula Non-thiol-comprising reducing agent 5% at pH 3.5 | Dye composition |
|---|---|---|---|---|
| Water | 89.0 | 98.36 | 94.75 | 95.5 |
| Pure thiolactic acid (Aldrich) | 8.0 | 1.0 | X | X |
| 2-Amino-2-methyl-1-propanol | 3.0 | 0.64 | X | X |
| Para-hydroxyphenol (Aldrich) | X | X | 5.0 | X |
| 0.1N HCl (Aldrich) | | | 0.25 | |
| Dye | X | X | X | 0.5 |

Example 2

Preparation of the Compositions

Composition A1:

Solution of thiolactic acid at 1% by weight at pH 3.5.

In a 150 ml flask 1 gram of thiolactic acid was added, then 50 grams of water was added and then 2-amino-2-methyl-1-propanol was added until a pH of the solution at 3.5 was obtained. It was then supplemented with water up to 100 grams and the final pH was checked (3.52).

Composition A2:

Solution of thiolactic acid at 1% by weight at pH 8.3.

In a 150 ml flask 1 gram of thiolactic acid was added, then 50 grams of water was added and then 2-amino-2-methyl-1-propanol was added until a pH of the solution at 8.3 was obtained. It was then supplemented with water up to 100 grams and the final pH was checked (8.32).

Composition B1:

Acid Red 18 dye solution at 0.5% by weight at spontaneous pH (pH=9.6)

Acid Red 18 dye of formula:

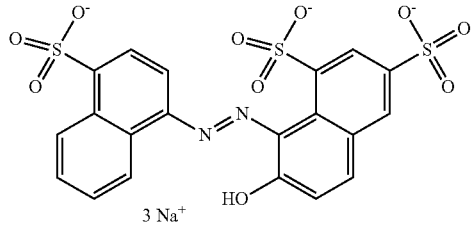 [SMILES: O=S(=O)([O-])c1cc(S(=O)(=O)[O-])c2c(/N=N/c3ccc(S(=O)(=O)[O-])c4ccccc34)c(O)ccc2c1]

In a 150 ml flask was introduced 0.5 gram of Acid red 18 dye and then 99.5 grams of water was added. The spontaneous pH was then measured after complete dissolution of the dye (spontaneous pH=9.62).

Composition C1:

para-hydroxyphenol solution at 5% by weight at pH 3.5.

In a 150 ml flask was introduced 5 grams of para-hydroxyphenol and then 50 grams of water was added. It was then added, dropwise, a solution of 1N hydrochloric acid until a pH of the solution at 3.5. It was then supplemented with water up to 100 grams and the final pH was checked (3.51).

Protocols

The following treatments were performed on 90% white natural hair locks.

Treatment 1:

A 1 gram lock is placed flat on a sheet of aluminum foil on a lock plate at 27° C. 2 grams of composition A1 were gently deposited along the lock and then applied with a coloring brush so as to have a homogeneous treatment. It was then left for 30 minutes and then wrung with KIMTECH paper. 2 grams of composition B1 was then deposited along the lock and then applied with a coloring brush to have a homogeneous treatment. It was then left for 20 minutes and then wrung with KIMTECH paper. 2 grams of composition C1 were then deposited along the lock and then applied with a coloring brush in order to have a homogeneous treatment. It was then left for 20 minutes and then wrung with KIMTECH paper. A blow-dry was then carried out at 80° C. (10 passes) and a hair straightening with straightening iron was carried out at 230° C. (10 passes in 6 seconds). A shampoo was then performed.

Treatment 2:

A 1 gram lock is placed flat on a sheet of aluminum foil on a lock plate at 27° C. 2 grams of composition A1 were gently deposited along the lock and then applied with a coloring brush so as to have a homogeneous treatment. It was then left for 30 minutes and then wrung with KIMTECH paper. 2 grams of composition C1 was then deposited along the lock and then applied with a coloring brush to have a homogeneous treatment. It was then left for 20 minutes and then wrung with KIMTECH paper. 2 grams of composition B1 were then deposited along the lock and then applied with a coloring brush in order to have a homogeneous treatment. It was then left for 20 minutes and then wrung with KIMTECH paper. A blow-dry was then carried out at 80° C. (10 passes) and a hair straightening with straightening iron was carried out at 230° C. (10 passes in 6 seconds). A shampoo was then performed.

Treatment 3:

A 1 gram lock is placed flat on a sheet of aluminum foil on a lock plate at 27° C. 2 grams of composition A2 were gently deposited along the lock and then applied with a coloring brush so as to have a homogeneous treatment. It was then left for 30 minutes and then wrung with KIMTECH paper. 2 grams of composition B1 was then deposited along the lock and then applied with a coloring brush to have a homogeneous treatment. It was then left for 20 minutes and then wrung with KIMTECH paper. 2 grams of composition C1 were then deposited along the lock and then applied with a coloring brush in order to have a homogeneous treatment. It was then left for 20 minutes and then wrung with KIMTECH paper. A blow-dry was then carried out at 80° C. (10 passes) and a hair straightening with straightening iron was carried out at 230° C. (10 passes in 6 seconds). A shampoo was then performed.

Treatment 4:

A 1 gram lock is placed flat on a sheet of aluminum foil on a lock plate at 27° C. 2 grams of composition A2 were gently deposited along the lock and then applied with a coloring brush so as to have a homogeneous treatment. It was then left for 30 minutes and then wrung with KIMTECH paper. 2 grams of composition C1 was then deposited along the lock and then applied with a coloring brush to have a homogeneous treatment. It was then left for 20 minutes and then wrung with KIMTECH paper. 2 grams of composition B1 were then deposited along the lock and then applied with a coloring brush in order to have a homogeneous treatment. It was then left for 20 minutes and then wrung with KIMTECH paper. A blow-dry was then carried out at 80° C. (10 passes) and a hair straightening with straightening iron was carried out at 230° C. (10 passes in 6 seconds). A shampoo was then performed.

The locks were then studied in a spectrophotometer to determine the color build-up $\Delta E^*$, representing the color uptake between the treated lock and the untreated lock ("color build-up" or "color uptake"), and the chromaticity $C^*$ (chromaticity).

The colour of the locks was evaluated in the CIE $L^*a^*b^*$ system using a Minolta Spectrophotometer CM3610D colorimeter. In this $L^*a^*b^*$ system, the three parameters respectively denote the intensity of the colour ($L^*$), the green/red colour axis ($a^*$) and the blue/yellow colour axis ($b^*$).

The lower the value of $L^*$, the darker or more intense the color. The higher the value of $a^*$, the redder the shade; the higher the value of $b^*$, the yellower the shade.

Color Build-Up:

The variation in colouration between the non-dyed and dyed locks of hair is defined by ($\Delta E^*$) according to the following equation:

$$\Delta E^* = \sqrt{(L^*-L_o^*)_2 + (a^*-a_o^*)^2 + (b^*-b_o^*)^2}$$

In this equation, $L^*$, $a^*$ and $b^*$ represent the values measured on locks of hair after dyeing and $L_o^*$, $a_o^*$ and $b_o^*$ represent the values measured on locks of hair before dyeing. The higher the value of $\Delta E^*$, the greater the colour build-up.

Chromaticity:

The chromaticity is calculated from the measurements of $a^*$ and of $b^*$ according to the following formula:

$$C^* = \sqrt{a^{*2}+b^{*2}}$$

The higher the value of $C^*$, the more chromatic is the colour.

The results are summarized in the table below:

| Treatments | L* | a* | b* | C* | ΔE* |
|---|---|---|---|---|---|
| 1 (Invention) | 45.93 | 19.29 | 12.64 | 23.06 | 21.02 |
| 2 (Invention) | 50.01 | 19.87 | 12.53 | 23.25 | 19.57 |
| 3 (Comparative) | 51.91 | 12.9 | 12.86 | 18.2 | 12.7 |
| 4 (Comparative) | 52.03 | 11.38 | 12.38 | 16.8 | 11.62 |

It appears from the above tests that the color build-up, the intensity and the chromaticity of the colorations obtained according to the process of the invention (treatments 1 and 2 with a composition A1 at pH=3.52), whatever the order of application of the dye and para-hydroxyphenol, are significantly better than the colorations obtained according to the comparative process (treatments 3 and 4 with a composition A2 at pH=8.32).

The invention claimed is:

1. Process for dyeing and relaxing the curls of keratin fibres, comprising:
   i) the application to said fibres of an acidic composition (A) having a pH between 1 and 5 and containing one or more thiol-comprising reducing agents;
   ii) the application to said fibres of a distinct composition (B) containing one or more dyes chosen from a) direct dyes and b) oxidation dyes; followed
   iii) by a step of heat treatment of the fibres by means of a heating tool;
   it being understood that steps i) and ii) are carried out separately, i.e. i) then ii) or else ii) then i) or together on the keratin fibres.

2. Process according to claim 1, comprising a step o) of using a composition (C) containing one or more non-thiol-comprising reducing agents after step i) and/or ii) and before the heat treatment step iii).

3. Process according to claim 1, characterized in that the thiol-comprising reducing agent(s) is (are) chosen from those of formulae i-1 and i-2, and also the organic or mineral acid or base salts thereof, optical isomers thereof and tautomers thereof, and the solvates:

$$R{-}SH \qquad \qquad \text{i-1}$$

$$R'S{-}R'' \qquad \qquad \text{i-2}$$

In which formulae i-1 and i-2:

R represents a linear or branched ($C_1$-$C_8$)alkyl, group which is optionally substituted, with one or more groups chosen from carboxy C(O)OH, (di)($C_1$-$C_4$)(alkyl) amino, hydroxyl —OH and thiol —SH, and/or optionally interrupted with one or more heteroatoms or groups chosen from —O—, —S—, —N(R′″)— wherein R′″ represents a hydrogen atom or a linear or branched ($C_1$-$C_4$)alkyl group, C(O) or combinations thereof;

a (hetero)aryl group optionally substituted in particular with one or more hydroxyl, thiol or carboxy groups;

R' and R", which may be identical or different, represent a $(C_1-C_8)$alkyl group, substituted with one or more groups chosen from hydroxyl, thiol and carboxy;

or else R' and R" form, together with the sulfur atom which bears them, a heterocyclic group, comprising from 5 to 7 ring members, which comprises from 1 to 3 heteroatoms, and which is optionally substituted.

4. Process according to claim 3, characterized in that the thiol-comprising reducing agent(s) is (are) chosen from those of formula i-1 for which R represents a linear or branched $(C_1-C_8)$alkyl group, substituted with one or more groups chosen from carboxy C(O)OH, amino, hydroxyl —OH, and thiol —SH;

and/or optionally interrupted with one or more heteroatoms or groups chosen from —O—, —N(R''')— wherein R''' represents a hydrogen atom or a linear or branched $(C_1-C_4)$alkyl group, C(O) or combinations thereof.

5. Process according to claim 3, characterized in that the thiol-comprising reducing agent(s) is (are) chosen from those of formula i-1 for which R represents:

a phenyl group optionally substituted with one or more hydroxyl, thiol or carboxy groups; or a heteroaryl comprising from 5 to 10 ring members, comprising from 1 to 4 heteroatoms chosen from 0, S or N, preferably N, optionally substituted with one or more hydroxyl or thiol groups.

6. Process according to claim 3, characterized in that the thiol-comprising reducing agent(s) is (are) chosen from those of formula i-2 for which R and R", which may be identical or different, represent a $(C_1-C_8)$alkyl group, substituted with one or more groups chosen from hydroxyl, thiol, and carboxy.

7. Process according to claim 1, characterized in that the thiol-comprising reducing agent(s) is (are) chosen from thioglycolic acid, thiolactic acid, cysteine, cysteamine, homocysteine, glutathione, thioglycerol, thiomalic acid, 2-mercaptopropionic acid, 3-mercaptopropionic acid, thiodiglycol, 2-mercaptoethanol, dithiothreitol, thioxanthine, thiosalicylic acid, thiodiglycolic acid, lipoic acid, N-acetylcysteine, and thioglycolic or thiolactic acid esters and amides, and mixtures of these compounds.

8. Process according claim 1, characterized in that the dye(s) is (are) chosen from a) direct dyes chosen from cationic and non-ionic, direct dyes.

9. Process according to claim 1, characterized in that the dyes are chosen from the following dyes:

mono- or dichromophore dyes having the formulae below:

$$A-(X)_p—C_{sat}—H \quad (XXVI)$$

$$A-(X)_p—C_{sat}—(X'')_{p'}-A' \quad (XXVI')$$

the organic or mineral acid salts, optical isomers and geometric isomers thereof, and the solvates;

in which formula (XXVI) or (XXVI'):

A, and A', which may be identical or different, represent a chromophore which is fluorescent and cationic or non-cationic;

X and X', which may be identical or different, represent a linear or branched, saturated or unsaturated $C_1-C_{30}$ hydrocarbon-based chain, optionally interrupted and/or optionally terminated at one or both of its ends with one or more divalent groups or heteroatoms or combinations thereof chosen from: —N(R)—, —O—, —S—, —C(O)—, —SO$_2$— with R, which may be identical or different, chosen from a hydrogen and a $C_1-C_4$ alkyl, hydroxyalkyl or aminoalkyl radical;

the indices p and p', which may be identical or different, are equal to 0 or 1;

$C_{sat}$, represents a linear or branched $C_1-C_{18}$ alkylene chain, optionally substituted, and/or optionally interrupted with one or more divalent groups or heteroatoms or combinations thereof chosen from: —N(R)—, —N$^+$(R)(R)—, —O—, —S—, —C(O)—, —SO$_2$— with R, which may be identical or different, chosen from a hydrogen and a $C_1-C_4$ alkyl, hydroxyalkyl or aminoalkyl radical;

the nitrobenzene direct dyes chosen from the compounds of formula (XXIX) below:

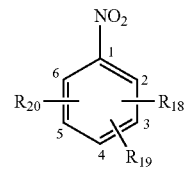

(XXIX)

In which formula (XXIX):

$R_{18}$ represents an amino radical; an amino radical monosubstituted or disubstituted with a $C_1-C_4$ alkyl, $C_1-C_4$ monohydroxyalkyl, $C_2-C_4$ polyhydroxyalkyl, $C_1-C_4$ aminoalkyl, mono($C_1-C_4$)alkylamino($C_1-C_4$)alkyl, di($C_1-C_4$)alkylamino($C_1-C_4$)alkyl, $C_1-C_4$ ureidoalkyl, aryl radical, aryl radical in which the aryl ring is substituted with one or more hydroxyl, carboxyl, amino or di($C_1-C_4$)alkylamino radicals;

$R_{19}$ represents a hydrogen atom; an amino radical; a hydroxyl radical; a $C_1-C_4$ alkyl radical; a $C_1-C_4$ alkoxy radical; a $C_1-C_4$ monohydroxyalkyl radical; a $C_2-C_4$ polyhydroxyalkyl radical; a $C_1-C_4$ monohydroxyalcoxy radical; a $C_2-C_4$ polyhydroxyalcoxy radical; a $C_1-C_4$ aminoalkoxy radical; an amino radical monosubstituted or disubstituted with a $C_1-C_4$ alkyl, $C_1-C_4$ monohydroxyalkyl, $C_2-C_4$ polyhydroxyalkyl, $C_1-C_4$ aminoalkyl, mono($C_1-C_4$)alkylamino($C_1-C_4$)alkyl, di($C_1-C_4$)alkylamino($C_1-C_4$)alkyl, $C_1-C_4$ ureidoalkyl, or aryl radical, in which aryl radical the aryl ring is substituted with one or more hydroxyl, carboxyl, amino or di($C_1-C_4$)alkylamino radicals; preferably;

$R_{20}$ represents a hydrogen or halogen atom, a $C_1-C_4$ alkyl radical or a nitro group.

10. Process according to claim 1, characterized in that the dye(s) is (are) chosen from the diaryl anionic azo dyes of formulae (II) or (III):

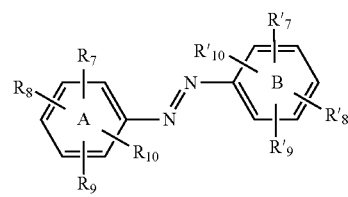

(II)

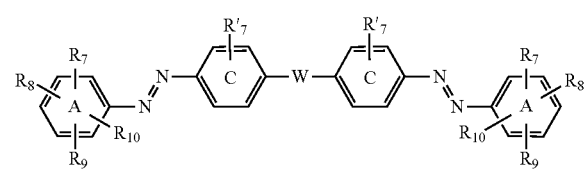

(III)

in which formulae (II) and (III):

$R_7$, $R_8$, $R_9$, $R_{10}$, $R'_7$, $R'_8$, $R'_9$ and $R'_{10}$, which may be identical or different, represent a hydrogen atom or a group chosen from:

alkyl;

alkoxy, alkylthio;

hydroxyl, mercapto;
nitro, nitroso;
$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
R"—$S(O)_2$—, with R" representing a hydrogen atom or an alkyl, aryl, (di)(alkyl)amino or aryl(alkyl)amino group;
R'"—$S(O)_2$—X'— with R'" representing an alkyl or optionally substituted aryl group, X' as defined previously;
(di)(alkyl)amino;
aryl(alkyl)amino optionally substituted with one or more groups chosen from i) nitro; ii) nitroso; iii) $(O)_2S(O^-)$—, $M^+$ and iv) alkoxy, with $M^+$ as defined previously;
optionally substituted heteroaryl;
cycloalkyl; in particular cyclohexyl;
Ar—N=N— with Ar representing an optionally substituted aryl group;
or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, M+; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N=N— and xi) optionally substituted aryl(alkyl)amino; with $M^+$, $R^o$, X, X', X" and Ar previously defined;
W represents a sigma bond σ, an oxygen or sulfur atom, or a divalent radical i) —NR— with R as defined previously, or ii) methylene —$C(R_a)(R_b)$— with $R_a$ and $R_b$, which may be identical or different, representing a hydrogen atom or an aryl group, or alternatively $R_a$ and $R_b$ form, with the carbon atom that bears them, a spiro cycloalkyl;
it being understood that formulae (II) and (III) comprise at least one sulfonate radical $(O)_2S(O^-)$—, $M^+$ or one carboxylate radical $(O)CO^-$—, $M^+$ on one of the rings A, A', B, B' or C.

11. Process according to claim 2, characterized in that the non-thiol-comprising reducing agent(s) is (are) chosen from ortho-diphenol derivatives of formula (XXXI)

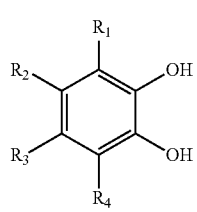

(XXXI)

in which formula (XXXI) the substituents:
$R_1$ to $R_4$, which may be identical or different, represent:
a hydrogen atom,
a halogen atom,
a hydroxyl radical,
a carboxyl radical;
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkoxy radical,
an alkoxyalkyl radical,
an alkoxyaryl radical,
an aryl radical,
a substituted aryl radical,
a saturated or unsaturated heterocyclic radical carrying or not carrying a cationic or anionic charge, optionally substituted and/or optionally fused with an aromatic ring, said aromatic ring being optionally substituted,
a radical containing one or more silicon atoms,
or two of the substituents carried by two adjacent carbon atoms $R_1$-$R_2$, $R_2$-$R_3$ or $R_3$-$R_4$ form, together with the carbon atoms carrying them, a saturated or unsaturated and aromatic or non-aromatic ring, optionally comprising one or more heteroatoms and optionally fused with one or more saturated or unsaturated rings optionally comprising one or more heteroatoms.

12. Process according claim 2, characterized in that the non-thiol-comprising reducing agent(s) is (are) chosen from meta-hydroxyphenol derivatives of formula (XXXII), and also the organic or mineral acid or base salts thereof, and the solvates thereof:

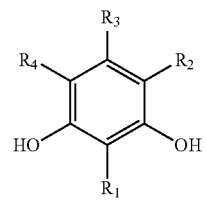

(XXXII)

in which formula (XXXII) the substituents:
$R_1$, $R_2$ and $R_4$, which may be identical or different, represent:
a hydrogen atom,
a halogen atom,
a carboxyl radical,
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkylcarbonyl radical,
a carboxaldehyde radical,
an alkoxy radical,
an alkoxyalkyl radical,
an alkoxyaryl radical,
an arylalkylcarbonyl radical of which the aryl group, optionally substituted,
an aryl radical,
a substituted aryl radical, a saturated or unsaturated heterocyclic radical carrying or not carrying a cationic or anionic charge, optionally substituted and/or optionally fused with an aromatic ring, said aromatic ring being optionally substituted, a radical containing one or more silicon atoms, $R_3$ represents:

a hydrogen atom, a halogen atom, a hydroxyl radical, a carboxyl radical, an alkyl carboxylate or alkoxycarbonyl radical, an optionally substituted amino radical, an optionally substituted and linear or branched alkyl radical, a linear or branched alkenyl radical which is optionally substituted, an optionally substituted cycloalkyl radical, an alkylcarbonyl radical, a carboxaldehyde radical, an alkoxy radical, an alkoxyalkyl radical, an alkoxyaryl radical, an aryl radical, a substituted aryl radical, a saturated or unsaturated heterocyclic radical carrying or not carrying a cationic or anionic charge, optionally substituted and/or optionally fused with an aromatic ring, preferably a benzene ring, said aromatic ring being optionally substituted, a radical containing one or more silicon atoms, or two of the substituents borne by two adjacent carbon atoms $R_2$-$R_3$ or $R_3$-$R_4$ form, together with the carbon atoms carrying them, a saturated or unsaturated and non-aromatic ring, optionally comprising one or more heteroatoms and optionally fused with one or more saturated or unsaturated rings optionally comprising one or more heteroatoms.

13. Process according to claim 2, characterized in that the non-thiol-comprising reducing agent(s) is (are) chosen from para-hydroxyphenol derivatives, of formula (XXXIII), and also the organic or mineral acid or base salts thereof, and the solvates thereof:

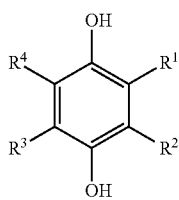

(XXXIII)

in which formula (XXXIII) $R^1$ to $R^4$, which may be identical or different, are as defined for formula (XXXI) or (XXXII).

14. Process according to claim 2, characterized in that the non-thiol-comprising reducing agent(s) is (are) chosen from catechol, gallic acid, para-hydroxyphenol, resveratrol and mixtures thereof.

15. Process according to claim 1, characterized in that the thiol-comprising reducing agent(s) represent(s) from 0.02% to 5% by weight relative to the total weight of the composition (A).

16. Process according to claim 1, characterized in that the dyeing agent(s) a) represent(s) at least 0.1% by weight, relative to the total weight of the composition.

17. Process according to claim 2, characterized in that the non-thiol-comprising reducing agent(s) represent(s) from 1% to 10% by weight relative to the total weight of the composition (C).

18. Process according to claim 2, characterized in that the ratio between the amount of thiol-comprising reducing agent(s) and the amount of non-thiol-comprising reducing agent(s) is between 0.1 and 5.

19. Process according to claim 1, characterized in that it comprises a step of rinsing the keratin fibres after step i) and/or step ii) and before the heat treatment step (iii).

20. Process according claim 1, characterized in that it comprises:

i) the application to the fibres of a composition (A) comprising said thiol-comprising reducing agent(s), then ii) the application to the fibres of a composition (B) comprising said direct dye(s), an optional step of rinsing the fibres, then iii) a step of heat treatment of the fibres by means of a heating tool.

21. Process according to claim 20, characterized in that it comprises, between steps i) and ii):

o) the application to the fibres of a composition (C) comprising said non-thiol-comprising reducing agent(s).

22. Process according to claim 1, characterized in that the heat treatment step iii) is carried out by means of a heating tool chosen from a hairstyling hood, a straightening iron, a hairdryer and an infrared-ray dispenser.

23. Process according to claim 1, characterized in that the heat treatment step is carried out at a temperature ranging from 30 to 250° C.

24. Acidic composition having a pH between 1 and 5, and containing one or more thiol-comprising reducing agents, and one or more dyes chosen from a) direct dyes and b) oxidation dyes in the absence of chemical oxidizing agent, and one or more non-thiol-comprising reducing agents.

25. Kit comprising at least two compartments:

a first compartment comprising an acidic composition (A), having a pH between 1 and 5, which comprises one or more thiol-comprising reducing agents, a second compartment comprising a composition (B) which comprises one or more direct dyes, and optionally a third compartment comprising a composition (C) which comprises one or more non-thiol-comprising reducing agents.

* * * * *

UNITED STATES PATENT AND TRADEMARK OFFICE
CERTIFICATE OF CORRECTION

PATENT NO. : 11,166,896 B2
APPLICATION NO. : 16/472824
DATED : November 9, 2021
INVENTOR(S) : V. Burckbuchler et al.

It is certified that error appears in the above-identified patent and that said Letters Patent is hereby corrected as shown below:

In the Claims

| Column | Line | |
|---|---|---|
| 55 | 25 | change "preferably N, optionally" to -- optionally --. |
| 55 | 29 | change "Rand" to -- R' and --. |
| 55 | 50 | change "(X")" to -- (X') --. |
| 55 | 62 | change "-N(R)-," to -- -N(R)-, -N$^+$(R)(R)-, --. |

Signed and Sealed this
Eighteenth Day of October, 2022

Katherine Kelly Vidal
*Director of the United States Patent and Trademark Office*